(12) United States Patent
Lachaine et al.

(10) Patent No.: US 9,974,977 B2
(45) Date of Patent: May 22, 2018

(54) IMAGE GUIDANCE FOR RADIATION THERAPY

(71) Applicant: Elekta, Inc., Atlanta, GA (US)

(72) Inventors: Martin Emile Lachaine, Montreal (CA); Fabienne Lathuiliere, Outremont (CA); Michel Moreau, Verona, WI (US)

(73) Assignee: Elekta, Inc., Atlanta, GA (US)

( * ) Notice: Subject to any disclaimer, the term of this patent is extended or adjusted under 35 U.S.C. 154(b) by 0 days. days.

(21) Appl. No.: 14/924,553

(22) Filed: Oct. 27, 2015

(65) Prior Publication Data
US 2016/0114192 A1     Apr. 28, 2016

Related U.S. Application Data

(60) Provisional application No. 62/069,145, filed on Oct. 27, 2014, provisional application No. 62/089,482, filed on Dec. 9, 2014.

(51) Int. Cl.
*G01D 18/00* (2006.01)
*A61N 5/10* (2006.01)
(Continued)

(52) U.S. Cl.
CPC ............ *A61N 5/1065* (2013.01); *A61B 5/055* (2013.01); *A61B 6/032* (2013.01); *A61B 8/085* (2013.01);
(Continued)

(58) Field of Classification Search
CPC ............ G06T 2207/10081; G06T 7/11; G06T 2207/10088; G06T 2207/10136;
(Continued)

(56) References Cited

U.S. PATENT DOCUMENTS 6,201,988 B1 *  3/2001  Bourland ............. A61N 5/1031
                                                              378/65
8,249,317 B2    8/2012  Falen et al.
(Continued)

FOREIGN PATENT DOCUMENTS

CN        107072628 A      8/2017
WO    WO-2016069633 A1    5/2016

OTHER PUBLICATIONS

"International Application Serial No. PCT/US2015/057633, International Search Report dated Feb. 10, 2016", 5 pgs.
(Continued)

*Primary Examiner* — Taeho Jo
(74) *Attorney, Agent, or Firm* — Schwegman Lundberg & Woessner, P.A.

(57) ABSTRACT

An adaptive therapy delivery system can receive imaging information including a volumetric image comprising a target such as a tumor or one or more other structures, and can receive imaging information corresponding to one or more imaging slices comprising different portions of the target, such as imaging slices acquired at different times after acquisition of the volumetric image. The system can spatially register information from an earlier-acquired image with a portion of the target included in a later-acquired one of the imaging slices. The system can then determine an updated location of the target indicated by the spatially-registered information. Using the updated location, the system can generate an updated therapy protocol to control delivery of a therapy beam.

32 Claims, 14 Drawing Sheets

(51) Int. Cl.
    *A61B 5/055* (2006.01)
    *A61B 6/03* (2006.01)
    *A61B 8/08* (2006.01)
    *G06T 7/33* (2017.01)
    *G06T 7/11* (2017.01)
    *A61B 90/00* (2016.01)
    *A61B 34/20* (2016.01)

(52) U.S. Cl.
    CPC ......... *A61N 5/1037* (2013.01); *A61N 5/1038* (2013.01); *A61N 5/1049* (2013.01); *G06T 7/11* (2017.01); *G06T 7/337* (2017.01); *A61B 2034/2065* (2016.02); *A61B 2090/367* (2016.02); *A61N 5/1039* (2013.01); *A61N 2005/1055* (2013.01); *A61N 2005/1058* (2013.01); *A61N 2005/1061* (2013.01); *G06T 2207/10081* (2013.01); *G06T 2207/10088* (2013.01); *G06T 2207/10132* (2013.01); *G06T 2207/20021* (2013.01); *G06T 2207/30096* (2013.01)

(58) Field of Classification Search
    CPC ....... G06T 2200/04; G06T 2207/10072; G06T 2207/10076; G06T 7/0016; G06T 2207/10132; G06T 2207/20021; G06T 2207/30096; A61N 5/1049; A61N 5/103; A61N 5/1002; A61N 5/1064; A61N 2005/1052; A61N 5/107; A61N 5/1071; A61N 2005/1058; A61N 5/1067; A61N 2005/1055; A61N 5/1038; A61N 5/1039; A61B 6/463; A61B 8/0833; A61B 8/085
    USPC ...................................................... 250/252.1
    See application file for complete search history.

(56) References Cited

U.S. PATENT DOCUMENTS

| | | | | |
|---|---|---|---|---|
| 2003/0112922 | A1* | 6/2003 | Burdette | A61B 6/5247 378/65 |
| 2004/0034301 | A1* | 2/2004 | Falco | A61B 8/08 600/427 |
| 2004/0042582 | A1* | 3/2004 | Ein-Gal | A61N 5/1049 378/8 |
| 2004/0106869 | A1* | 6/2004 | Tepper | A61B 8/0833 600/443 |
| 2005/0054916 | A1* | 3/2005 | Mostafavi | A61B 6/504 600/427 |
| 2005/0080332 | A1* | 4/2005 | Shiu | A61B 6/032 600/411 |
| 2005/0090733 | A1* | 4/2005 | Van Der Lugt | A61B 5/055 600/411 |
| 2005/0180544 | A1* | 8/2005 | Sauer | A61N 5/1049 378/195 |
| 2005/0182316 | A1* | 8/2005 | Burdette | A61B 8/0833 600/424 |
| 2005/0251029 | A1* | 11/2005 | Khamene | A61B 8/4245 600/427 |
| 2006/0064014 | A1* | 3/2006 | Falco | A61B 8/0833 600/439 |
| 2006/0274061 | A1* | 12/2006 | Wang | A61N 5/103 345/420 |
| 2007/0021669 | A1 | 1/2007 | Miga et al. | |
| 2007/0053491 | A1* | 3/2007 | Schildkraut | A61N 5/1049 378/65 |
| 2007/0064867 | A1* | 3/2007 | Hansen | A61B 5/0091 378/37 |
| 2007/0167699 | A1* | 7/2007 | Lathuiliere | G06T 7/0083 600/407 |
| 2008/0031404 | A1* | 2/2008 | Khamene | A61B 6/032 378/6 |
| 2008/0109013 | A1* | 5/2008 | Fu | A61B 6/032 606/130 |
| 2008/0317305 | A1* | 12/2008 | Cover | G06T 5/50 382/128 |
| 2009/0003512 | A1* | 1/2009 | Pouliot | A61B 6/466 378/4 |
| 2009/0175406 | A1 | 7/2009 | Zhang et al. | |
| 2009/0180589 | A1* | 7/2009 | Wang | A61N 5/10 378/65 |
| 2009/0264753 | A1* | 10/2009 | von Schulthess | A61B 5/0263 600/431 |
| 2009/0275830 | A1* | 11/2009 | Falco | A61B 8/08 600/437 |
| 2010/0067739 | A1* | 3/2010 | Mostafavi | G06T 7/285 382/103 |
| 2011/0019896 | A1* | 1/2011 | Fu | A61N 5/1049 382/132 |
| 2011/0103551 | A1* | 5/2011 | Bal | A61N 5/103 378/65 |
| 2011/0103657 | A1* | 5/2011 | Kang | G06K 9/6215 382/128 |
| 2011/0116701 | A1* | 5/2011 | Zhu | G06T 7/38 382/131 |
| 2012/0008734 | A1* | 1/2012 | Thomson | G06T 7/0014 378/4 |
| 2012/0014501 | A1* | 1/2012 | Pelc | A61B 6/025 378/9 |
| 2012/0035462 | A1* | 2/2012 | Maurer, Jr. | A61B 6/5247 600/411 |
| 2012/0076269 | A1* | 3/2012 | Roberts | A61N 5/1049 378/65 |
| 2012/0155734 | A1* | 6/2012 | Barratt | G06T 7/344 382/131 |
| 2012/0294497 | A1* | 11/2012 | Zankowski | A61N 5/1038 382/128 |
| 2014/0105355 | A1* | 4/2014 | Toimela | A61N 5/103 378/41 |
| 2014/0275962 | A1* | 9/2014 | Foo | A61N 2/002 600/411 |
| 2016/0113614 | A1* | 4/2016 | Cetingul | G06T 11/006 382/131 |

OTHER PUBLICATIONS

"International Application Serial No. PCT/US2015/057633, Written Opinion dated Feb. 10, 2016", 6 pgs.

Cervino, Laura I., et al., "MRI-guided tumor tracking in lung cancer radiotherapy", Phys. Med. Biol. 56, (2011), 3773-3786.

Dellaert, Frank, et al., "Fast Image-Based Tracking by Selective Pixel Integration", Proceedings of the ICCV Workshop on Frame Rare Vision, (1999), 22 pgs.

Kirilova, Anna, et al., "Three-Dimensional Motion of Liver Tumors Using Cine-Magnetic Resonance Imaging", Int. J. Radiation Oncology Biol. Phys, vol. 71, No. 4, (2008), 1189-1195.

Zhuang, Ling, et al., "An optimization algorithm for 3D real-time lung tumor tracking during arc therapy using kV projection images", The International Journal of Medical Physics Research and Practice, Medical Physics 40, 101710, (2013), 11 pgs.

"International Application Serial No. PCT/US2015/057633, International Preliminary Report on Patentability dated May 11, 2017", 8 pgs.

"Australian Application Serial No. 2015339388, First Examiners Report dated Sep. 30, 2017", 4 pgs.

"European Application Serial No. 15791169.4, Response filed Dec. 12, 2017 to Communication pursuant to Rules 161(1) and 162 EPC dated Jun. 2, 2017", 44 pgs.

* cited by examiner

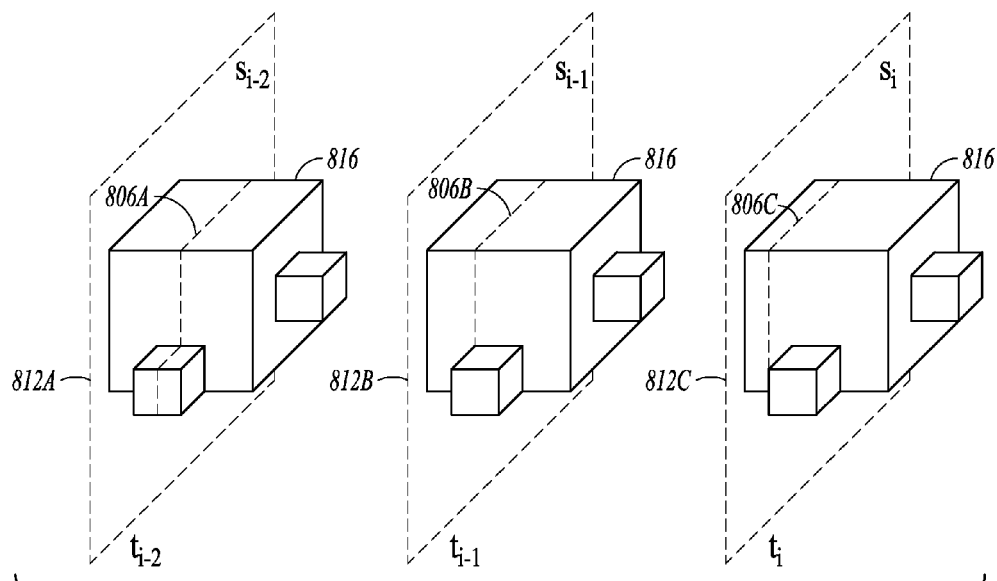
FIG. 8A
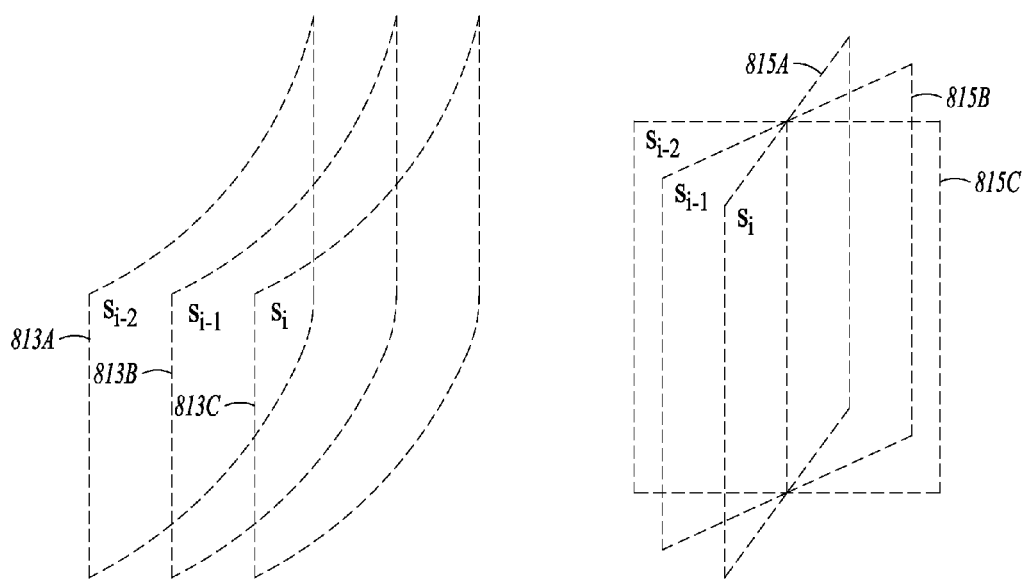
FIG. 8B     FIG. 8C

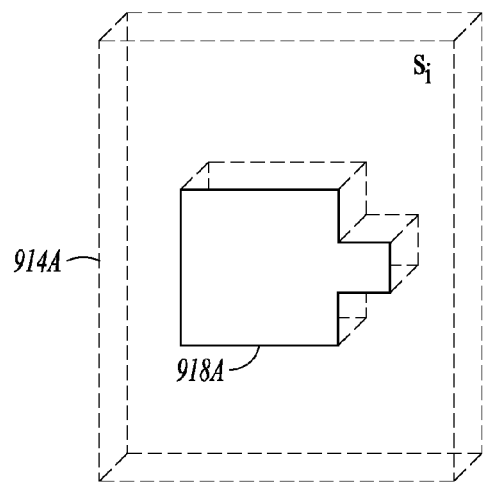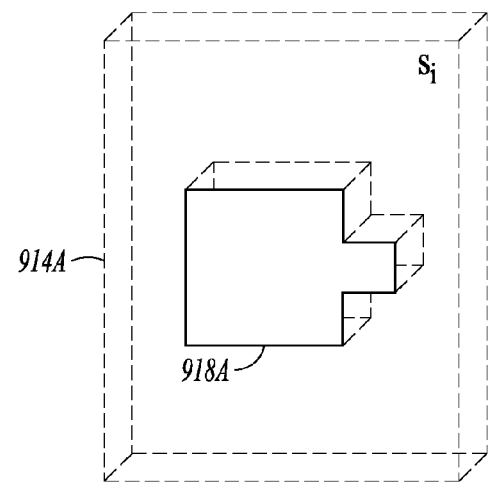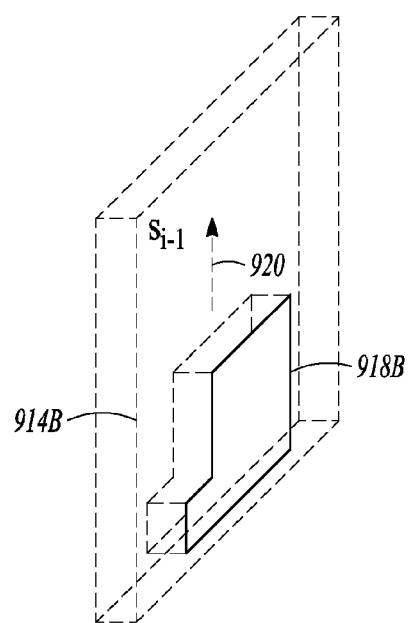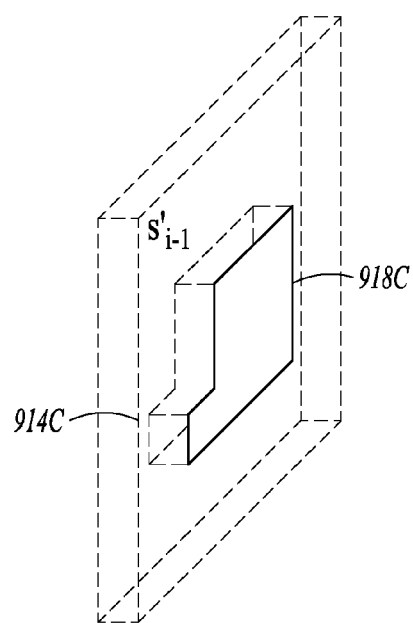
*FIG. 9A*        *FIG. 9B*

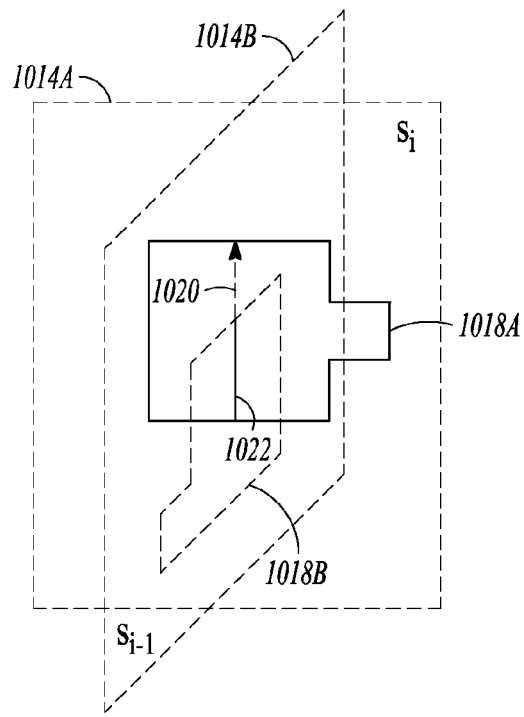
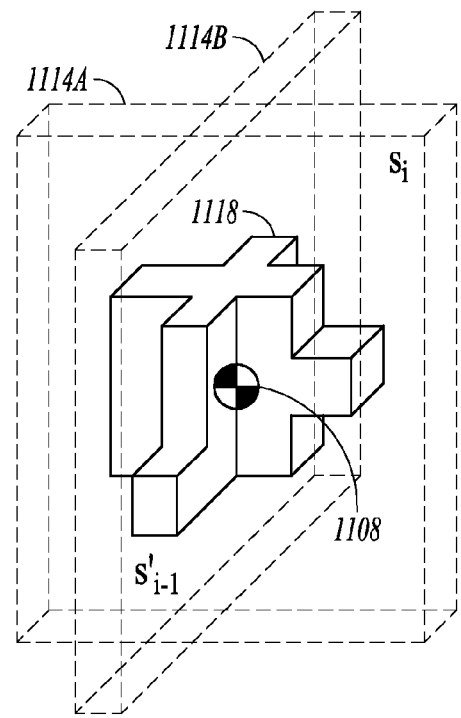
FIG. 10          FIG. 11A
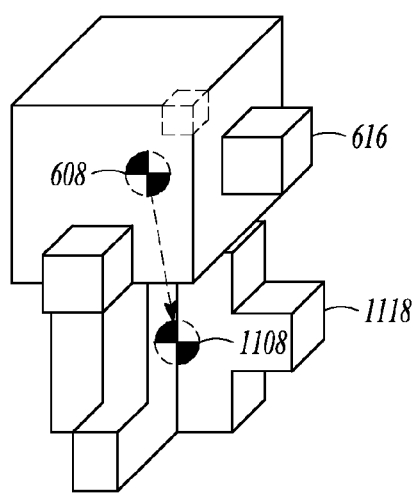
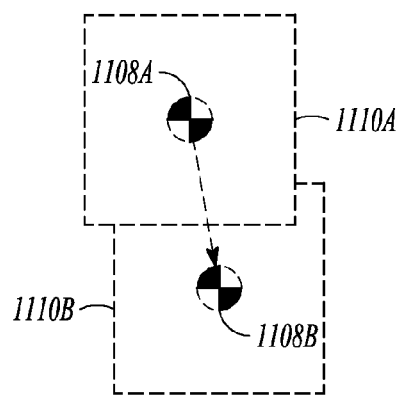
FIG. 11B         FIG. 11C

IMAGE GUIDANCE FOR RADIATION THERAPY

CLAIM OF PRIORITY

This patent application claims the benefit of priority of (1) Moreau, U.S. Provisional Patent Application Ser. No. 62/069,145, titled "MRI-LINAC REAL-TIME IMAGE GUIDANCE TECHNIQUES," filed on Oct. 27, 2014; and (2) Lachaine et al., U.S. Provisional Patent Application Ser. No. 62/089,482, titled "MAGNETIC RESONANCE IMAGING TARGET LOCALIZATION," filed on Dec. 9, 2014; each of which is hereby incorporated by reference herein in its entirety.

TECHNICAL FIELD

This disclosure generally relates to radiation therapy or radiotherapy. More specifically, the disclosure relates to systems and methods for adapting a radiation therapy treatment plan in order to compensate for changes in a position of a target tumor during the delivery of radiation therapy.

BACKGROUND

Radiation therapy or "radiotherapy" can be used to treat cancers or other ailments in mammalian (e.g., human and animal) tissue. One such radiotherapy technique is a Gamma Knife, by which a patient is irradiated by a large number of low-intensity gamma rays that converge with high intensity and high precision at a target (e.g., a tumor). In another embodiment, radiotherapy is provided using a linear accelerator, whereby a tumor is irradiated by high-energy particles (e.g., electrons, protons, ions, high-energy photons, and the like). The placement and dose of the radiation beam must be accurately controlled to ensure the tumor receives the prescribed radiation, and the placement of the beam should be such as to minimize damage to the surrounding healthy tissue, often called the organ(s) at risk (OARs). Radiation is termed "prescribed" because a physician orders a predefined amount of radiation to the tumor and surrounding organs similar to a prescription for medicine.

Generally, ionizing radiation in the form of a collimated beam is directed from an external radiation source toward a patient.

A specified or selectable beam energy can be used, such as for delivering a diagnostic energy level range or a therapeutic energy level range. Modulation of a radiation beam can be provided by one or more attenuators or collimators (e.g., a multi-leaf collimator). The intensity and shape of the radiation beam can be adjusted by collimation avoid damaging healthy tissue (e.g., organs at risk) adjacent to the targeted tissue by conforming the projected beam to a profile of the targeted tissue.

The treatment planning procedure may include using a three-dimensional image of the patient to identify a target region (e.g., the tumor) and to identify critical organs near the tumor. Creation of a treatment plan can be a time consuming process where a planner tries to comply with various treatment objectives or constraints (e.g., dose volume histogram (DVH) objectives), taking into account their individual importance (e.g., weighting) in order to produce a treatment plan that is clinically acceptable. This task can be a time-consuming trial-and-error process that is complicated by the various organs at risk (OARs) because as the number of OARs increases (e.g., up to thirteen for a head-and-neck treatment), so does the complexity of the process. OARs distant from a tumor may be easily spared from radiation, while OARs close to or overlapping a target tumor may be difficult to spare.

Traditionally, for each patient, the initial treatment plan can be generated in an "offline" manner. The treatment plan can be developed well before radiation therapy is delivered, such as using one or more medical imaging techniques. Imaging information can include, for example, images from X-rays, Computed Tomography (CT), nuclear magnetic resonance (MR), positron emission tomography (PET), single-photon emission computed tomography (SPECT), or ultrasound. A health care provider, such as a physician, may use three-dimensional imaging information indicative of the patient anatomy to identify one or more target tumors along with the organs at risk near the tumor. The health care provider can delineate the target tumor that is to receive a prescribed radiation dose using a manual technique, and the health care provider can similarly delineate nearby tissue, such as organs, at risk of damage from the radiation treatment. Alternatively or additionally, an automated tool (e.g., ABAS provided by Elekta AB, Sweden) can be used to assist in identifying or delineating the target tumor and organs at risk. A radiation therapy treatment plan ("treatment plan") can then be created using an optimization technique based on clinical and dosimetric objectives and constraints (e.g., the maximum, minimum, and mean doses of radiation to the tumor and critical organs).

The treatment planning procedure may include using a three-dimensional image of the patient to identify a target region (e.g., the tumor) and to identify critical organs near the tumor. Creation of a treatment plan can be a time consuming process where a planner tries to comply with various treatment objectives or constraints (e.g., dose volume histogram (DVH) objectives), taking into account their individual importance (e.g., weighting) in order to produce a treatment plan that is clinically acceptable. This task can be a time-consuming trial-and-error process that is complicated by the various organs at risk (OARs) because as the number of OARs increases (e.g., up to thirteen for a head-and-neck treatment), so does the complexity of the process. OARs distant from a tumor may be easily spared from radiation, while OARs close to or overlapping a target tumor may be difficult to spare.

The treatment plan can then be later executed by positioning the patient and delivering the prescribed radiation therapy. The radiation therapy treatment plan can include dose "fractioning," whereby a sequence of radiation therapy deliveries are provided over a predetermined period of time (e.g., 45 fractions), with each therapy delivery including a specified fraction of a total prescribed dose. However, during treatment the position of the patient and the position of the target tumor in relation to the treatment machine (e.g., linear accerator—"linac") is very important in order to ensure the target tumor and not healthy tissue is irradiated.

OVERVIEW

The present inventors have recognized, among other things, that a radiation therapy treatment plan can be adjusted contemporaneously in an adaptive manner in order to compensate for changes in a position of a target tumor during the delivery or radiation therapy to the tumor. For example, a desired target, such as a tumor, can shift in position to such an extent that if an exclusively "offline" approach to therapy planning is used, a location of the tumor indicated by medical images taken prior to treatment can be significantly different from the location of the tumor target during radiation therapy treatment. For example, the tumor may shrink, may move, or can be misaligned compared to the expected or desired location as indicated in the treatment plan. Motion of the target can be caused by one or more sources, such as heart motion, respiration, a reflex such as a cough, or other movements. Therefore, the position of where radiation therapy should be delivered based on images taken prior to treatment can be significantly misaligned with the desired target when the radiation therapy is eventually delivered. Hereinafter, a "target locus" is a location of the target such as prior to treatment, and "a therapy locus" is a location where radiation therapy is delivered during treatment (and ideally is aligned with the actual location of the target at the time of radiation therapy delivery).

In one approach, imaging can be performed contemporaneously with the delivery of a radiation therapy, such as performing an imaging acquisition immediately before initiating radiation therapy delivery during a treatment session, or using a sequence of respective therapy delivery followed by immediately acquiring one or more images of the tumor during a radiation therapy delivery session. Such imaging can provide information helpful for identifying a position of the target or for identifying the motion of the target. Such contemporaneous imaging can be referred to generically as "real-time," but in general a latency or time delay exists between an acquisition of an image and a delivery of radiation therapy, which is generally on the order of about 100 to 500 milliseconds (ms).

A problem exists if an acquisition latency or imaging acquisition rate of three-dimensional volumetric imaging information is unacceptable (e.g., imaging acquisition is too slow to permit therapy guidance or control, such as greater than about 500 ms for respiratory targets). The subject matter described herein can address such a problem, such as by facilitating more rapid acquisition of imaging slices (including one or more of one-dimensional profiles, two-dimensional slices, or three-dimensional volumes comprising a sub-volume or sub-region of an earlier-imaged volumetric region), including comparing information indicative of a portion of the target locus obtained rapidly from one or more imaging slices to information obtained from an earlier-acquired volumetric reference image.

In an example, an adaptive image-guided therapy delivery system can receive imaging information including a volumetric image comprising a target within a radiation therapy patient, and can receive imaging information corresponding to one or more imaging slices comprising different portions of the target, the imaging slices acquired at different instants after acquisition of the volumetric image.

According to various examples, the system can spatially register information indicative of a portion of the target from at least one of the imaging slices acquired earlier as well as spatially registering a portion of the target from at least one of the imaging slices acquired at a later time. The system can then determine a difference between a location of the target indicated by the spatially-registered information and an earlier location of the target indicated by the earlier-acquired volumetric image. The system can then generate an updated therapy protocol to control delivery of a therapy beam based on the determined difference in the position of the target.

In another example, a portion or entirety of a volumetric reference image can be spatially registered with one or more imaging slices, such as to determine an optimal shift between the volumetric reference image and one or more imaging slices. For example, the volumetric reference image can include three-dimensional imaging information (e.g., grayscale or contrast values corresponding to voxels), and the three-dimensional imaging information can be translated or rotated to achieve an optimal registration with one or more imaging slices (e.g., two-dimensional imaging information). A goodness-of-fit between the shifted or rotated three-dimensional volumetric imaging information and one or more imaging slices can include use of one or more metrics, without requiring segmentation of the target.

An updated therapy protocol can be generated in an adaptive manner to align the therapy locus established by the therapy beam with an updated target locus or to gate the beam so that the therapy is delivered when the therapy locus passes through the target locus. Updating a therapy protocol can include one or more of (a) adjustment of actuators coupled to a moveable platform such as a couch or table supporting the therapy recipient, (b) adjustment of one or more apertures configured to collimate or shape the therapy beam, (c) adjustment of one or more actuators configured to position a therapy output to establish a specified therapy beam direction, or (d) gating of therapy delivery such as using obtained imaging or information from other sensors, as illustrative examples.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

FIG. 8A illustrates generally a series of imaging acquisition planes, such as can be obtained as a target locus moves from one imaging acquisition instance to another.

FIG. 8B illustrates generally a series of imaging acquisition regions, such as can include a curved shape.

FIG. 8C illustrates generally a series of imaging acquisition planes, such as can include different orientations that need not each be orthogonal to the others.

FIG. 9A illustrates generally a series of two imaging slices, such as including a target locus that is displaced between first and second imaging slices.

FIG. 9B illustrates generally a series of two spatially-registered imaging slices, such as after a segmented portion of the target locus is adjusted in one or more of the imaging slices.

FIG. 10 illustrates generally a technique that can include spatially registering segmented portions of a target locus.

FIG. 11A illustrates generally a composite segmented representation of a target locus, such as after spatial registration of portions of the target locus acquired at different times.

FIG. 11B illustrates generally a technique for determining a difference between a location of the target locus according to acquired spatially-registered imaging information as compared to an earlier location of the target locus such as represented by earlier-acquired volumetric imaging information.

FIG. 11C illustrates generally a technique for updating a therapy protocol, such as to shift a therapy locus to a new location.

Figure 1A:
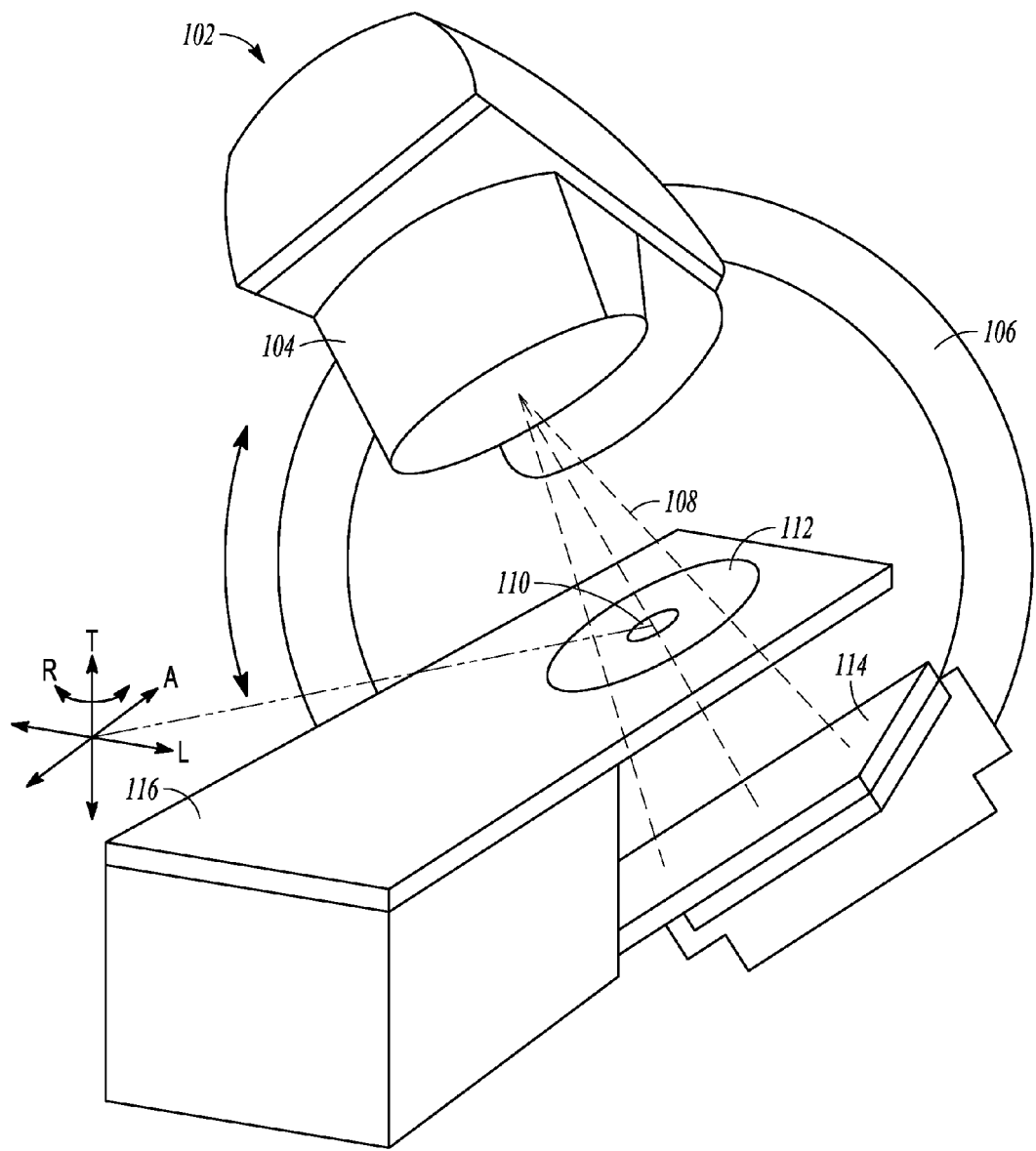
FIG. 1A illustrates generally an example of a radiation therapy system that can include radiation therapy output configured to provide a therapy beam.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

FIG. 1A illustrates generally an example of a radiation therapy system 102 that can include radiation therapy output 104 configured to provide a therapy beam 108. The radiation therapy output 104 can include one or more attenuators or collimators, such as a multi-leaf collimator (MLC) as described in the illustrative example of FIG. 2. Referring back to FIG. 1A, a patient can be positioned in a region 112, such as on a platform 116 (e.g., a table or a couch), to receive a radiation therapy dose according to a radiation therapy treatment plan. The radiation therapy output 104 can be located on a gantry 106 or other mechanical support, such as to rotate the therapy output 104 around an axis ("A"). One or more of the platform 116 or the radiation therapy output 104 can be moveable to other locations, such as moveable in transverse direction ("T") or a lateral direction ("L"). Other degrees of freedom are possible, such as rotation about one or more other axes, such as rotation about a transverse axis (indicated as "R").

The coordinate system (including axes A, T, and L) shown in FIG. 1A can have an origin located at an isocenter 110. The isocenter can be defined as a location where the radiation therapy beam 108 intersects the origin of a coordinate axis, such as to deliver a prescribed radiation dose to a location on or within a patient. For example, the isocenter 110 can be defined as a location where the radiation therapy beam 108 intersects the patient for various rotational positions of the radiation therapy output 104 as positioned by the gantry 106 around the axis A.

In an example, a detector 114 can be located within a field of the therapy beam 108, such as can include a flat panel detector (e.g., a direct detector or a scintillation-based detector). The detector 114 can be mounted on the gantry 106 opposite the radiation therapy output 104, such as to maintain alignment with the therapy beam 108 as the gantry 106 rotates. In this manner, the detector 114 can be used to monitor the therapy beam 108 or the detector can be used 114 for imaging, such as portal imaging.

In an illustrative example, one or more of the platform 116, the therapy output 104, or the gantry 106 can be automatically positioned, and the therapy output 104 can establish the therapy beam 108 according to a specified dose for a particular therapy delivery instance. A sequence of therapy deliveries can be specified according to a radiation therapy treatment plan, such as using one or more different orientations or locations of the gantry 106, platform 116, or therapy output 104. The therapy deliveries can occur sequentially, but can intersect in a desired therapy locus on or within the patient, such as at the isocenter 110. A prescribed cumulative dose of radiation therapy can thereby be delivered to the therapy locus while damage to tissue nearby the therapy locus is reduced or avoided.

As mentioned in relation to other examples herein, the radiation therapy system 102 can include or can be coupled to an imaging acquisition system, such as to provide one or more of nuclear magnetic resonance (MR) imaging, X-ray imaging, such as can include computed tomography (CT) imaging, or ultrasound imaging. In an example, MR imaging information or other imaging information can be used to generate imaging information or visualizations equivalent to CT imaging, without requiring actual CT imaging. Such imaging can be referred to as "pseudo-CT" imaging.

Figure 1B:
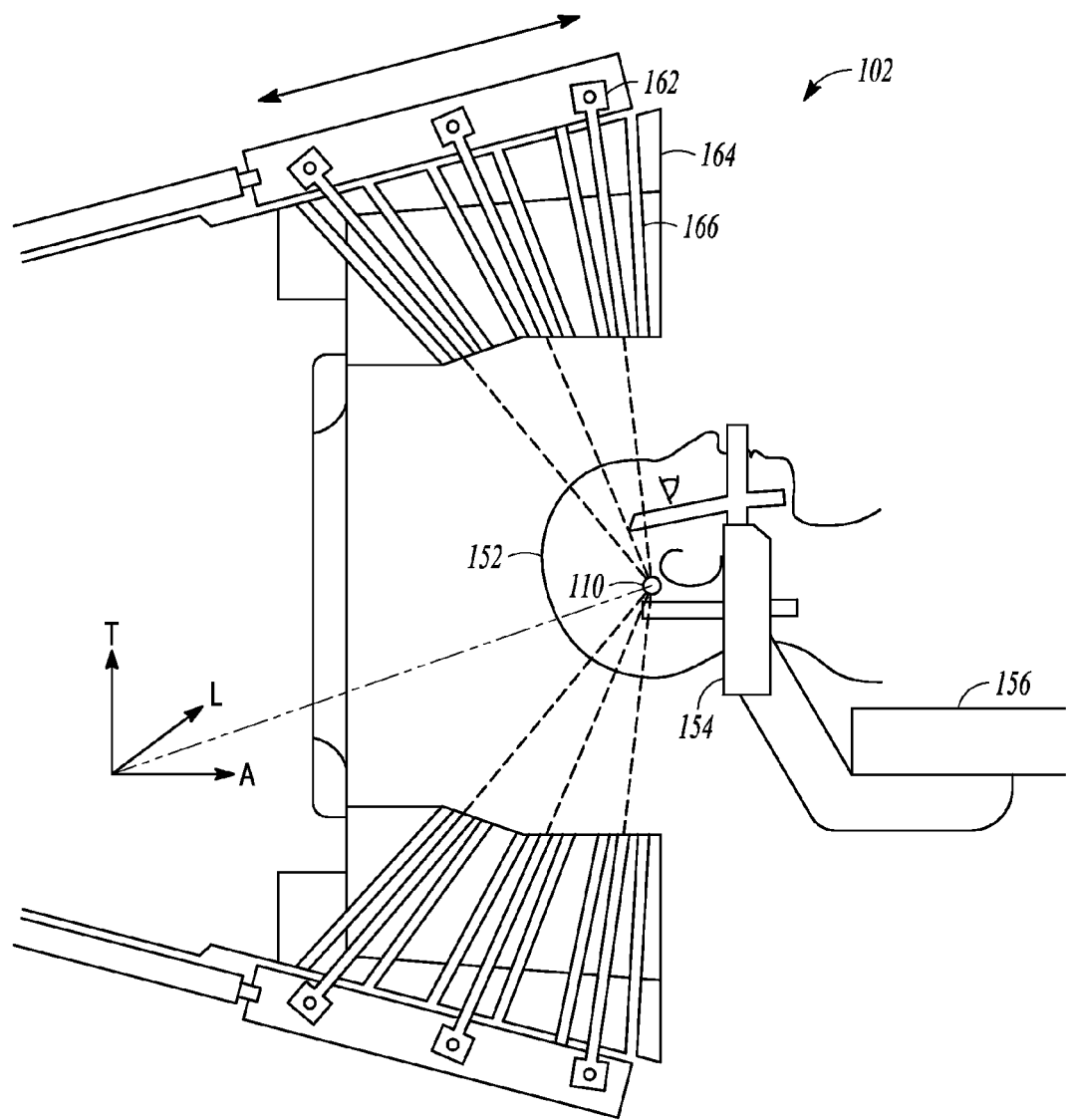
FIG. 1B illustrates generally another example of a radiation therapy system.

FIG. 1B illustrates generally another example of a radiation therapy system 102 (e.g., Leksell Gamma Knife manufactured by Elekta, AB, Stockholm, Sweden), according to some embodiments of the present disclosure. As shown in FIG. 1B, in a radiation therapy treatment session, a patient 152 may wear a coordinate frame 154 to stabilize a portion of the patient's anatomy (e.g., the head) undergoing surgery or radiation therapy. Coordinate frame 154 and a patient positioning system 156 may establish a spatial coordinate system, which may be used while imaging a patient or during radiation surgery.

Radiation therapy device 102 may include a protective housing 164 to enclose a plurality of radiation sources 162.

Radiation sources 162 may generate a plurality of radiation beams (e.g., beamlets) through beam channels 166. The plurality of radiation beams may be configured to focus on an isocenter 158 from different directions. While each individual radiation beam may have a relatively low intensity, isocenter 158 may receive a relatively high level of radiation when multiple doses from different radiation beams accumulate at isocenter 158. In certain embodiments, isocenter 158 may correspond to a target under surgery or treatment, such as a tumor.

Figure 1C:
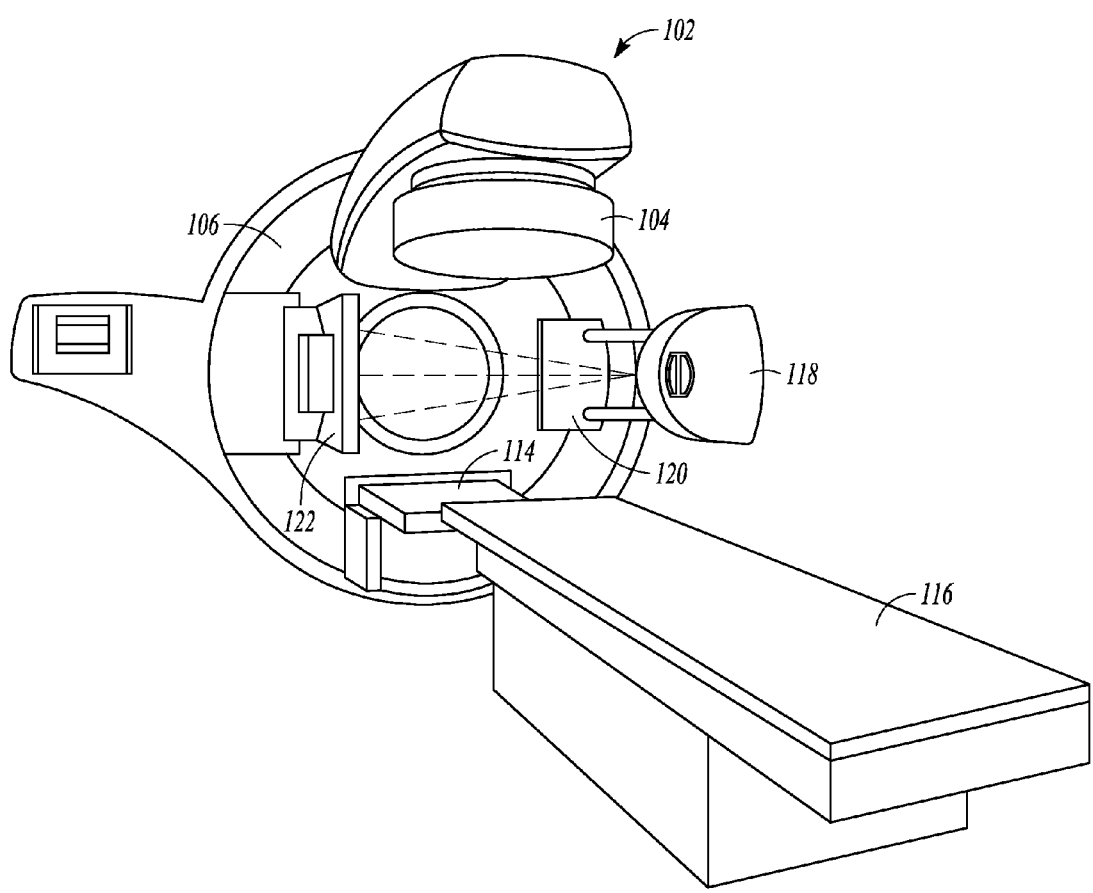
FIG. 1C illustrates generally an example of a system that can include a combined radiation therapy system and an imaging system, such as can include a computed tomography (CT) imaging system.

FIG. 1C illustrates generally an example of a system that can include a combined radiation therapy system 102 and an imaging system, such as can include a computed tomography (CT) imaging system. The CT imaging system can include an imaging X-ray source 118, such as providing X-ray energy in a kiloelectron-Volt (keV) energy range. The imaging X-ray source 118 provides one or more of fan-shaped or conical beam 120 directed to an imaging detector 122, such as a flat panel detector. The radiation therapy system 102 can be similar to the system 102 described in relation to FIG. 1A, such as including a radiation therapy output 104, a gantry 106, a platform 116, and another flat panel detector 114. As in the examples of FIG. 1A, FIG. 1B, and FIG. 1D, the radiation therapy system 102 can be coupled to, or can include, a high-energy accelerator configured to provide a therapeutic radiation beam. The X-ray source 118 can provide a comparatively-lower-energy X-ray diagnostic beam, for imaging.

In the illustrative example of FIG. 1C, the radiation therapy output 104 and the X-ray source 118 can be mounted on the same rotating gantry 106, rotationally-separated from each other by 90 degrees. In another example, two or more X-ray sources can be mounted along the circumference of the gantry 106, such as each having its own detector arrangement to provide multiple angles of diagnostic imaging concurrently. Similarly, multiple radiation therapy outputs 104 can be provided.

Figure 1D:
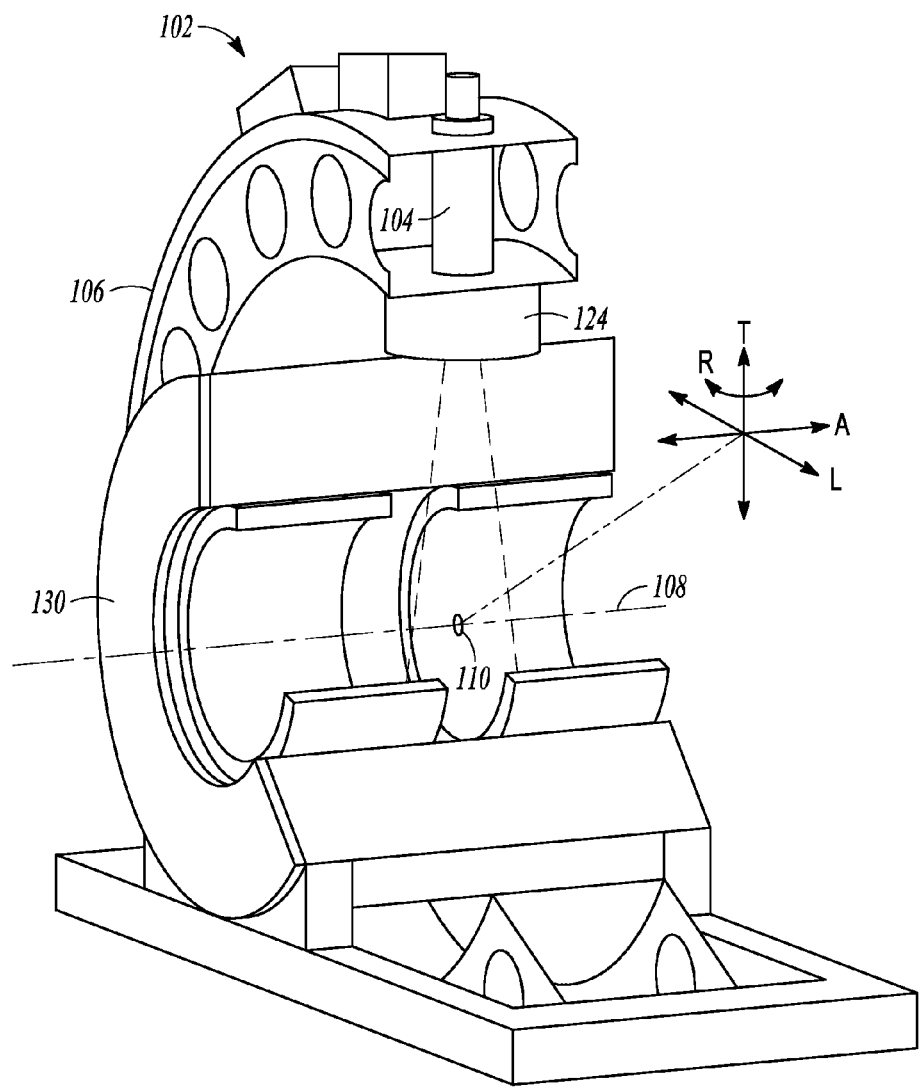
FIG. 1D illustrates generally a partially cut-away view of an example of a system that can include a combined radiation therapy system and an imaging system, such as can include a nuclear magnetic resonance (MR) imaging system.

FIG. 1D illustrates generally a partially cut-away view of an example of a system that can include a combined radiation therapy system 102 and an imaging system, such as can include a nuclear magnetic resonance (MR) imaging system 130. The MR imaging system 130 can be arranged to define a "bore" around an axis ("A"), and the radiation therapy system can include a radiation therapy output 104, such as to provide a radiation therapy beam 108 directed to an isocenter 110 within the bore along the axis, A. The radiation therapy output 104 can include a collimator 124, such as to one or more of control, shape, or modulate radiation therapy beam 108 to direct the beam 108 to a therapy locus aligned with a desired target locus within a patient. The patient can be supported by a platform, such as a platform positionable along one or more of an axial direction, A, a lateral direction, L, or a transverse direction, T. One or more portions of the radiation therapy system 102 can be mounted on a gantry 106, such as to rotate the radiation therapy output 104 about the axis A.

FIG. 1A, FIG. 1B, FIG. 1C, and FIG. 1D illustrate generally examples including a configuration where a therapy output can be rotated around a central axis (e.g., an axis "A"). Other radiation therapy output configurations can be used. For example, a radiation therapy output can be mounted a robotic arm or manipulator, such as having multiple degrees of freedom. In yet another example, the therapy output can be fixed, such as located in a region laterally separated from the patient, and a platform supporting the patient can be used to align a radiation therapy isocenter with a specified target locus within the patient.

Figure 2:
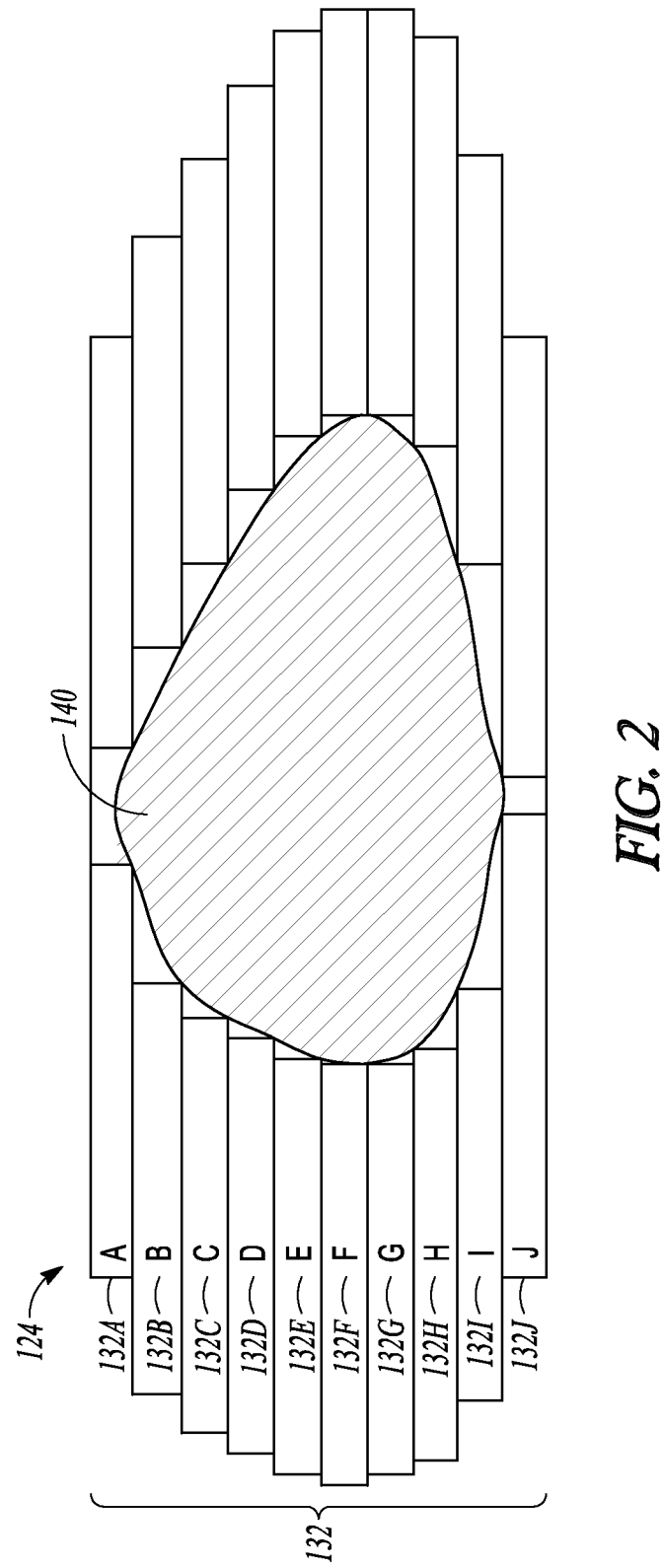
FIG. 2 illustrates generally an example of a collimator configuration, such as can be used to one or more of shape, direct, or modulate an intensity of a radiation therapy beam.

FIG. 2 illustrates generally an example of a multi-leaf collimator (MLC) 132, such as can be used to one or more of shape, direct, or modulate an intensity of a radiation therapy beam. In FIG. 2, leaves 132A through 132J can be automatically positioned to define an aperture approximating a tumor 140 cross section or projection. The leaves 132A through 132J can be made of a material specified to attenuate or block the radiation beam in regions other than the aperture, in accordance with the radiation treatment plan. For example, the leaves 132A through 132J can include metallic plates, such as comprising tungsten, with a long axis of the plates oriented perpendicular to a beam direction, and having ends oriented parallel to the beam direction (as shown in the plane of the illustration of FIG. 2). A "state" of the MLC 132 can be adjusted adaptively during a course of radiation therapy, such as to establish a therapy beam that better approximates a shape or location of the tumor 140 or other target locus, as compared to using a static collimator configuration or as compared to using an MLC 132 configuration determined exclusively using an "offline" therapy planning technique. A radiation therapy technique including using the MLC 132 to produce a specified radiation dose distribution to a tumor or to specific areas within a tumor can be referred to as Intensity Modulated Radiation Therapy (IMRT).

Figure 3:
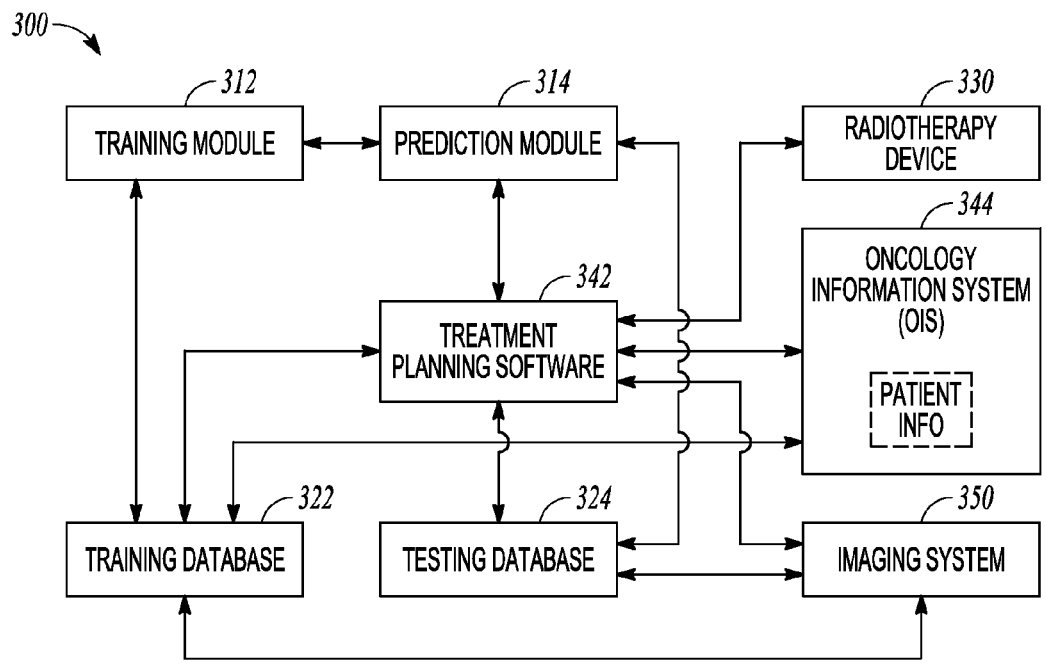
FIG. 3 illustrates generally an example of radiation therapy system, such as can include a radiation therapy device and an imaging acquisition device.

FIG. 3 illustrates generally an example of radiation therapy system 300, such as can include a radiation therapy device 330 and an imaging acquisition device. Radiation therapy system 300 may include a training module 312, a prediction module 314, a training database 322, a testing database 324, a radiation therapy device 330, and an image acquisition device 350. Radiation therapy system 300 may also be connected to a treatment planning system (TPS) 342 and an oncology information system (OIS) 344, which may provide patient information. In addition, radiation therapy system 300 may include a display device and a user interface.

Figure 4:
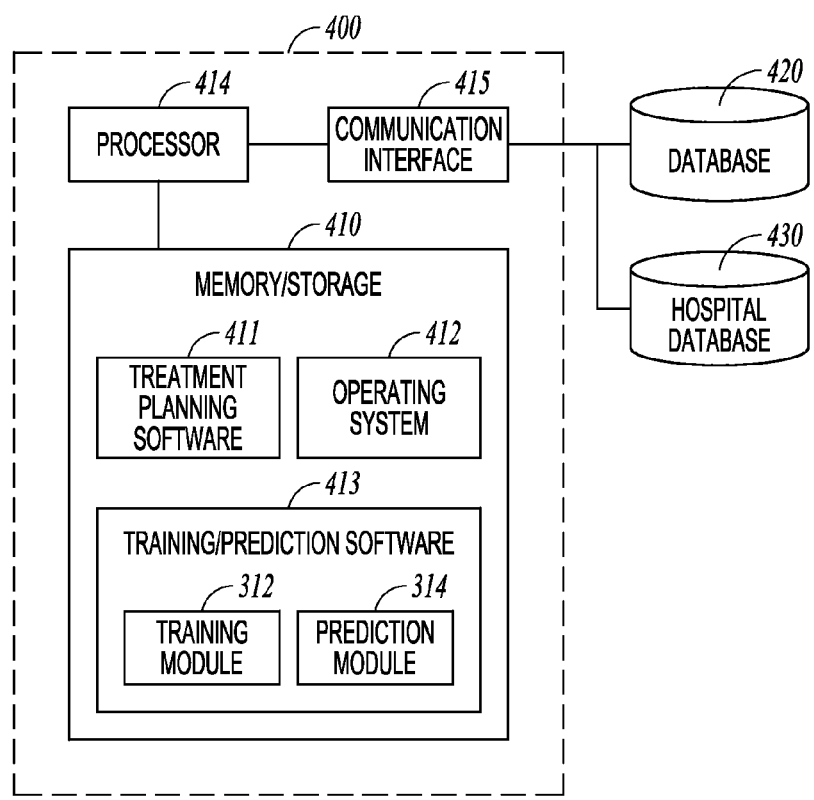
FIG. 4 illustrates generally an example of a system that can be used for one or more of imaging acquisition, image segmentation, target prediction, therapy control, or therapy adjustment.

FIG. 4 illustrates generally an example of a system 400 that can be used for one or more of imaging acquisition, image segmentation, target prediction, therapy control, or therapy adjustment. According to some embodiments, system 400 may be one or more high-performance computing devices capable of identifying, analyzing, maintaining, generating, or providing large amounts of data consistent with the disclosed embodiments. System 400 may be standalone, or it may be part of a subsystem, which in turn may be part of a larger system. For example, system 400 may represent distributed high-performance servers that are remotely located and communicate over a network, such as the Internet, or a dedicated network, such as a local area network (LAN) or a wide-area network (WAN). In some embodiments, system 400 may include an embedded system, imaging scanner (e.g., a nuclear magnetic resonance (MR) scanner or other scanner such as a computed tomography (CT) scanner), and/or touch-screen display device in communication with one or more remotely located high-performance computing devices.

In one embodiment, system 400 may include one or more processors 414, one or more memories 410, and one or more communication interfaces 415. Processor 414 may be a processor circuit, including one or more general-purpose processing devices such as a microprocessor, central processing unit (CPU), graphics processing unit (GPU), or the like. More particularly, processor 414 may be a complex instruction set computing (CISC) microprocessor, reduced instruction set computing (RISC) microprocessor, very long instruction Word (VLIW) microprocessor, a processor implementing other instruction sets, or processors implementing a combination of instruction sets.

Processor 414 may also be one or more special-purpose processing devices such as an application specific integrated circuit (ASIC), a field programmable gate array (FPGA), a digital signal processor (DSP), a System-on-a-Chip (SoC), or the like. As would be appreciated by those skilled in the art, in some embodiments, processor 414 may be a special-purpose processor, rather than a general-purpose processor. Processor 414 may include one or more known processing devices, such as a microprocessor from the Pentium™ or Xeon™ family manufactured by Intel™ the Turion™ family manufactured by AMD™, or any of various processors manufactured by other vendors such as Oracle™ (e.g., a SPARC™-architecture processor). Processor 414 may also include graphical processing units manufactured by Nvidia™. The disclosed embodiments are not limited to any type of processor(s) otherwise configured to meet the computing demands of identifying, analyzing, maintaining, generating, and/or providing large amounts of imaging data or any other type of data consistent with the disclosed embodiments.

Memory 410 may include one or more storage devices configured to store computer-executable instructions used by processor 414 to perform functions related to the disclosed embodiments. For example, memory 410 may store computer executable software instructions for treatment planning software 411, operating system software 412, and training/prediction software 413. Processor 414 may be communicatively coupled to the memory/storage device 410, and the processor 414 may be configured to execute the computer executable instructions stored thereon to perform one or more operations consistent with the disclosed embodiments. For example, processor 414 may execute training/prediction software 413 to implement functionalities of training module 312 and prediction module 314. In addition, processor device 414 may execute treatment planning software 411 (e.g., such as Monaco® provided by Elekta) that may interface with training/prediction software 413.

The disclosed embodiments are not limited to separate programs or computers configured to perform dedicated tasks. For example, memory 410 may include a single program that performs the functions of the system 400 or multiple programs (e.g., treatment planning software 411 and/or training/prediction software 413). Additionally, processor 414 may execute one or more programs located remotely from system 400, such as programs stored in database 420, such remote programs may include oncology information system software or treatment planning software. Memory 410 may also store image data or any other type of data/information in any format that the system may use to perform operations consistent with the disclosed embodiments.

Communication interface 415 may be one or more devices configured to allow data to be received and/or transmitted by system 400. Communication interface 415 may include one or more digital and/or analog communication devices that allow system 400 to communicate with other machines and devices, such as remotely located components of system 400, database 420, or hospital database 430. For example, Processor 414 may be communicatively connected to database(s) 420 or hospital database(s) 430 through communication interface 415. For example, Communication interface 415 may be a computer network, such as the Internet, or a dedicated network, such as a LAN or a WAN. Alternatively, the communication interface 415 may be a satellite communications link or any form of digital or analog communications link that allows processor 414 to send/receive data to/from either database(s) 420, 430.

Database(s) 420 and hospital database(s) 430 may include one or more memory devices that store information and are accessed and managed through system 400. By way of example, database(s) 420, hospital database(s) 530, or both may include relational databases such as Oracle™ databases, Sybase™ databases, or others and may include non-relational databases, such as Hadoop sequence files, HBase, Cassandra or others. The databases or other files may include, for example, one or more of raw data from MR scans or CT scans associated with an imaging subject, such as for training or providing a reference image, MR feature vectors, CT values, reduced-dimension feature vectors, pseudo-CT prediction model(s), pseudo-CT value(s), pseudo-CT image, DICOM data, etc. Systems and methods of disclosed embodiments, however, are not limited to separate databases. In one aspect, system 400 may include database(s) 420 or hospital database(s) 430. Alternatively, database(s) 420 and/or hospital database(s) 430 may be located remotely from the system 400. Database(s) 420 and hospital database(s) 430 may include computing components (e.g., database management system, database server, etc.) configured to receive and process requests for data stored in memory devices of database(s) 420 or hospital database(s) 430 and to provide data from database(s) 420 or hospital database(s) 430.

System 400 may communicate with other devices and components of system 400 over a network (not shown). The network may be any type of network (including infrastructure) that provides communications, exchanges information, or facilitates the exchange of information and enables the sending and receiving of information between other devices and/or components of system 400 over a network (not shown). In other embodiments, one or more components of system 400 may communicate directly through a dedicated communication link(s), such as a link (e.g., hardwired link, wireless link, or satellite link, or other communication link) between system 400 and database(s) 420 and hospital database(s) 430.

The configuration and boundaries of the functional building blocks of system 400 has been defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments.

Figure 5:
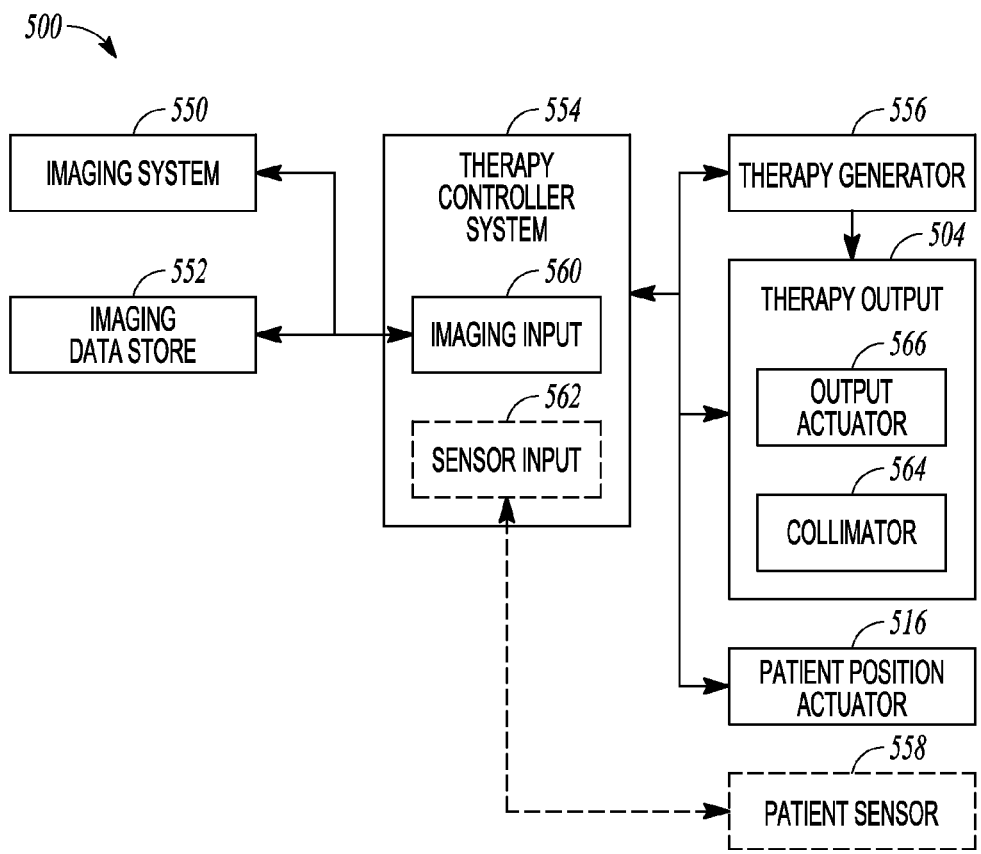
FIG. 5 illustrates generally an example of a system, such as can include a radiation therapy controller having an imaging input, a radiation therapy generator, and a radiation therapy output.

FIG. 5 illustrates generally an example of a system 500, such as can include a radiation therapy controller system 554 having an imaging input 560, a radiation therapy generator 556, and a radiation therapy output 504. The therapy generator 556 can include an accelerator, such as a linear accelerator, or another source of radiation, and the therapy output 504 can be coupled to the therapy generator 556 to process a beam of energetic photons or particles provided by the therapy generator 556. For example, the therapy output 504 can include or can be coupled to an output actuator 566 to one or more of rotate or translate the therapy output 504 to provide a radiation therapy beam having a therapy locus directed to a desired target locus. The therapy output 504 can include a collimator 564, such as a multi-leaf collimator as mentioned above in relation to FIG. 2. Referring back to FIG. 5, the therapy controller system 554 can be configured to control one or more of the therapy generator 556, the therapy output 504, or a patient position actuator 516 (such as a movable platform including a couch or table), using an adaptive radiation treatment technique as described in other examples herein.

The therapy controller system 554 can be coupled to one or more sensors, such as using a sensor input 562. For example, a patient sensor 558 can provide physiologic information to the therapy controller system, such as information indicative of one or more of respiration (e.g., using a plethysmographic sensor), patient cardiac mechanical or electrical activity, peripheral circulatory activity, patient position, or patient motion. Such information can provide a surrogate signal correlated with motion of one or more organs or other regions to be targeted by the therapy output 504, and such information can be used to control therapy (e.g., for therapy gating).

The imaging input 560 can be coupled to an imaging system 550 (such as can include a computed tomography imaging system, a nuclear magnetic resonance (MR) imaging system, or an ultrasound imaging system, as illustrative examples). Alternatively, or in addition, the therapy controller system 554 can receive imaging information from an imaging data store 552, such as a centralized imaging database or imaging server. One or more of the therapy controller system 554 or the imaging system 550 can include elements shown and described in relation to the system 400 shown in FIG. 4.

Figure 6:
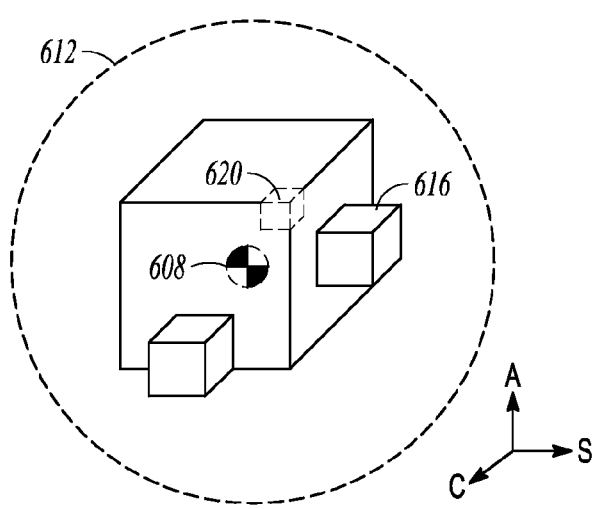
FIG. 6 illustrates generally a view of a target locus, such as a tumor region, such as can be obtained using a volumetric imaging technique.

FIG. 6 illustrates generally a view of a target locus 616, such as a tumor region to be treated using radiation therapy. Information indicative of the target locus 616 can be obtained using a volumetric imaging technique. The representation in FIG. 6 is shown has having rectangular facets merely for purposes of illustration, and an actual target locus 616 may include curved or irregular surfaces. A region of interest 612 can be imaged, such as using one or more of MR imaging, CT imaging, pseudo-CT image visualization, portal imaging, ultrasound imaging, or other techniques. The target locus 616 can be identified such as using automated, manual, or semi-automated image segmentation techniques. For example, a specified label can be assigned to voxels (e.g., a voxel 620) to identify a locus or group of voxels comprising a radiation therapy target. As an illustrative example, a contrast value for a voxel 620 can be compared to adjacent voxels, and an edge of a tumor or other region can be identified such as using contrast information. Other regions can also be identified such as nearby organs or locations of other features.

Various features of the target locus can be determined such as one or more edge locations (e.g., using an edge detection or edge identification technique). For example, a position of the target locus 616 can be identified by determining a spatial centroid 608 of the target locus 616. The use of a centroid 608 as an extracted feature is illustrative and other features can be used for tracking target locus 616 motion, such as a manually-identified or automatically-determined location of a point, surface, or edge of the target locus 616. In yet another example, an implantable or external seed fiducial can be used, such as providing an indicium in obtained imaging information.

The target locus 616 and one or more corresponding features such as the centroid 608 can be identified during treatment planning imaging, such as inter-fractionally (e.g., between radiation therapy delivery sessions) or just prior to beginning a radiation therapy delivery session. Volumetric imaging information comprising the target locus 616 can be referred to as a "reference image." As mentioned above, a challenge can exist because image acquisition and processing latency may preclude "real time" acquisition of volumetric imaging information during radiation treatment. Accordingly, intra-fractional image acquisition (such as during or between radiation therapy deliveries in a radiation therapy session) can include more rapid acquisition of imaging slices (including one or more of one-dimensional profiles, two-dimensional slices, or three-dimensional volumes comprising a sub-volume or sub-region of an earlier-imaged volumetric region). Information indicative of a portion of the target locus obtained rapidly from one or more imaging slices can be compared to information obtained from an earlier-acquired volumetric reference image to update a therapy protocol, such as to adjust therapy due to movement of the target locus. The imaging modality used for obtaining or generating the volumetric reference image need not be the same as is used for intra-fractional imaging.

In another example, the target locus 616 need not be segmented or otherwise identified in the volumetric reference image. Use of the phrase "target locus" is merely illustrative of a target within the region of interest such as a portion or an entirety of a tumor to be treated or other anatomical structures such as organs near the tumor. In addition to, or instead of segmentation of the target locus 616, various techniques as described herein can be performed such as including spatially registering a portion of the volumetric reference image (e.g., a specified region of interest) or an entirety of the volumetric reference image with other imaging information such as using voxel values including contrast or grayscale values. For example, such spatial registration can include three-dimensional (e.g. volumetric) registration with one or more two-dimensional imaging slices (e.g., 3D-to-2D registration), or other techniques.

Figure 7A:
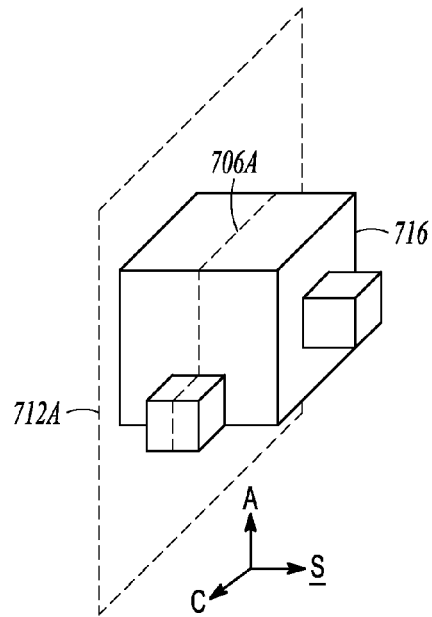
FIG. 7A and FIG. 7B illustrate views of an imaging acquisition plane (in FIG. 7A) and a corresponding acquired imaging slice (in FIG. 7B) corresponding to a first imaging plane orientation.
Figure 7B:
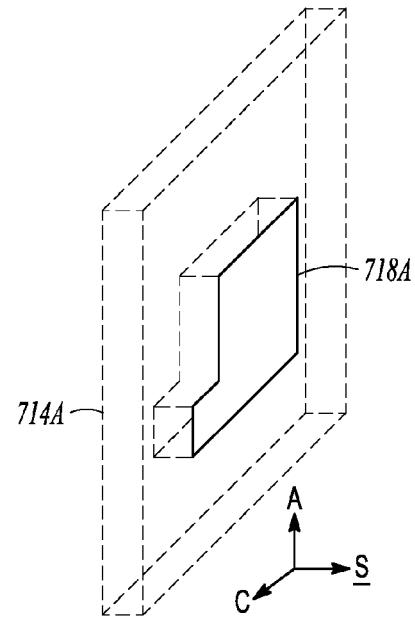

FIG. 7A and FIG. 7B illustrate views of an imaging acquisition plane 712A (in FIG. 7A) of a target locus 716 and a corresponding acquired imaging slice 714A (in FIG. 7B) corresponding to a first imaging plane orientation intersecting the target locus 716 along a line 706A. As an illustrative example, FIG. 7A can represent a sagittal orientation of the image acquisition plane 712A and corresponding slice 714A. An imaging "slice" can include two-dimensional pixel imaging information or three-dimensional imaging information, such as having a small finite thickness as shown illustratively in FIG. 7B. A portion 718A of the target locus in the imaging slice 714A can be identified, such as again using a segmentation technique, for example using a discrete dynamic contour, snake, or level set, or a registration-based technique.

Figure 7C:
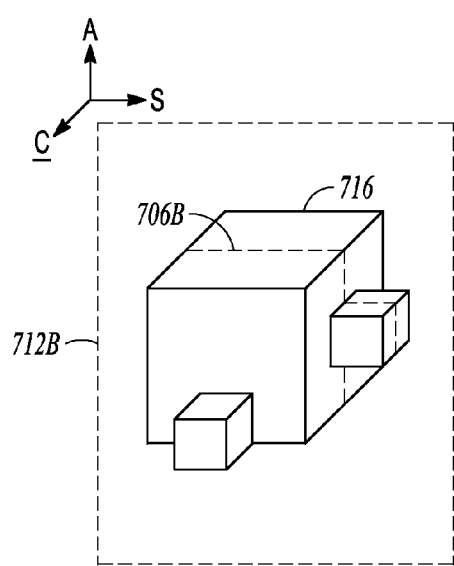
FIG. 7C and FIG. 7D illustrate views of an imaging acquisition plane (in FIG. 7C) and a corresponding acquired imaging slice (in FIG. 7D) corresponding to a second imaging plane orientation, such as can be orthogonal to the first imaging plane orientation mentioned above in relation to FIG. 7A and FIG. 7B.
Figure 7D:
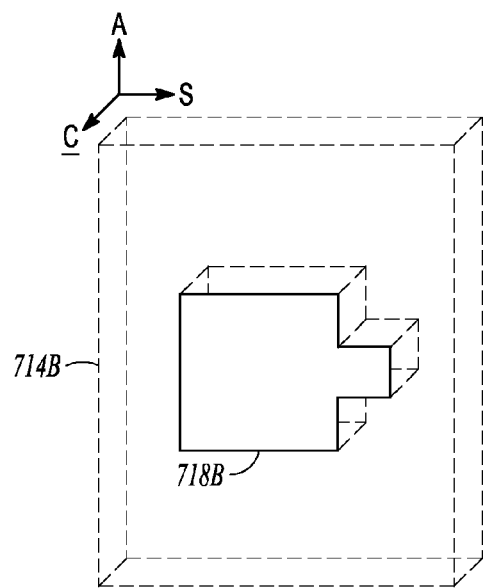
Figure 7E:
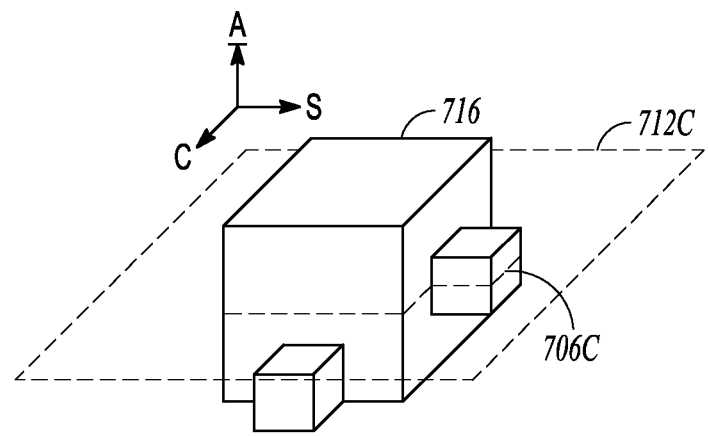
FIG. 7E and FIG. 7F illustrate views of an imaging acquisition plane (in FIG. 7E) and a corresponding acquired imaging slice (in FIG. 7F) corresponding to a third imaging plane orientation, such as can be orthogonal to one or more of the first and second imaging plane orientations mentioned above in relation to FIG. 7A, FIG. 7B, FIG. 7C, and FIG. 7D.
Figure 7F:
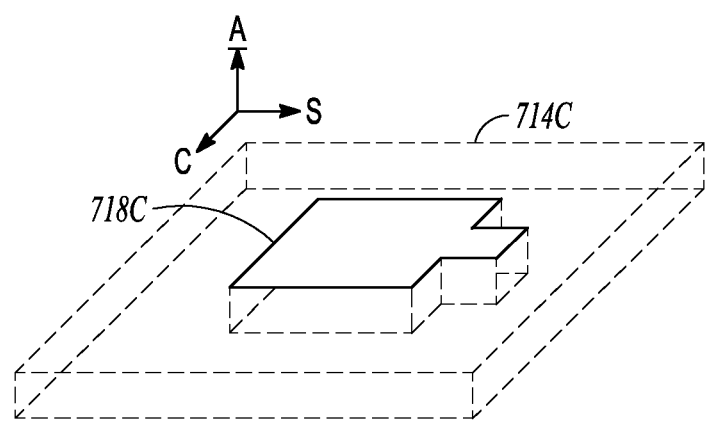

A series of imaging slices can be obtained, such as including different imaging acquisition plane orientations as shown in FIG. 7C, FIG. 7D, FIG. 7E, and FIG. 7F. For example, FIG. 7C and FIG. 7D illustrate views of an imaging acquisition plane 712B (in FIG. 7C) intersecting the target locus 716 along a line 706B and a corresponding acquired imaging slice 714B (in FIG. 7D) including a different portion 718B of the target locus 716, corresponding to a second imaging plane orientation, such as can be orthogonal to the first imaging plane orientation mentioned above in relation to FIG. 7A and FIG. 7B. As an illustration, FIG. 7C and FIG. 7D can correspond to a coronal plane. FIG. 7E and FIG. 7F illustrate views of an imaging acquisition plane 712C (in FIG. 7E) intersecting the target locus 716 along a line 706C and a corresponding acquired imaging slice 714C (in FIG. 7F) including yet another different portion 718C of the target locus 716, corresponding to a third imaging plane orientation, such as can be orthogonal to one or more of the first and second imaging plane orientations mentioned above in relation to FIG. 7A, FIG. 7B, FIG. 7C, and FIG. 7D. As an illustration, FIG. 7E and FIG. 7F can correspond to an axial imaging plane. The imaging slices of FIG. 7A, FIG. 7B, FIG. 7C, FIG. 7D, FIG. 7E, and FIG. 7F are shown as two-dimensional planes that are orthogonal to each other. However, as mentioned in relation to other examples herein, the slices need not be planar nor orthogonal. Each acquired imaging slice can be processed, including processing of one or more slices in parallel with an acquisition of an imaging slice. For example, such processing can include sampled information from a volumetric reference image, such as corresponding to a plane or region of the acquired imaging slice.

In one approach, a feature extracted from one or more of the imaging slices 714A, 714B, or 714C can be compared with imaging information extracted from a volumetric reference image. For example, a segmented portion of the target locus 616 from the volumetric reference image, or a region encapsulating the target locus and surrounding tissues, can be spatially registered with a corresponding imaging slice 714A, 714B, or 714C to determine if the target locus has shifted. However, comparing a feature extracted from a single two-dimensional imaging slice with a corresponding feature from the volumetric reference image can present challenges. For example, FIG. 8A illustrates generally a series of imaging acquisition planes 812A, 812B, and 812C, such as can be obtained as a target locus 816 moves from one imaging acquisition instance to another. At time $t_{i-2}$, a line 806A where the imaging acquisition plane intersects the target locus 816 is roughly centered, and at time $t_{i-1}$, the line 806B is shifted, and at time $t_i$, the line 806C is shifted further. Imaging slices obtained at times $t_i$, $t_{i-1}$, $t_{i-2}$, . . . can be labeled as $S_i$, $S_{i-1}$, $S_{i-2}$, . . . generally.

If the motion of the target locus is out-of-plane, the centroid or other feature location may not appear to shift significantly from image-to-image, even though the target locus has moved significantly, or the target locus may appear to deform making interpretation of motion difficult. However, such out-of-plane motion can be properly tracked such as by one or more of varying an orientation of successively-acquired imaging slices (e.g., as shown in FIG. 8C and elsewhere), or varying or compensating for a non-planar shape of the imaging acquisition region so that the imaging slices are not represented as perfectly planar in a three-dimensional sense (e.g., as shown in FIG. 8B). For example, FIG. 8B illustrates generally a series of imaging slices 813A, 813B, and 813C, such as can include a curved shape. Generally, even when referring to image acquisition "planes," the techniques described herein can be used with other slice geometries such as the curved slices of FIG. 8B. As an illustrative example, MR imaging information may be available as planar slices, and a transformation can be applied to the planar slices to obtain surfaces that curve in a three-dimensional sense, such as to help capture or correct for distortion across the imaging field such as to compensate for inhomogeneity in an established magnetic field. As another illustrative example, FIG. 8C illustrates generally a series of imaging acquisition planes 815A, 815B, and 815C such as can include different orientations that need not each be orthogonal.

As mentioned above, if imaging slices are acquired sequentially in time, the target locus is likely to shift between successive image acquisitions. FIG. 9A illustrates generally a series of two imaging slices, such as including a target locus that is displaced between first and second imaging slices. The example of two sequentially-acquired imaging slices is illustrative. The techniques described herein are also generally applicable to sequences of more than two imaging slices (or even a single imaging slice analyzed with respect to a portion or an entirety of the reference volumetric imaging information).

An imaging slice 914A (e.g., Si) can include a portion 918A of the target locus, and a second imaging slice 914B ($S_{i-1}$, such as acquired earlier in time) can include a second portion 918B. The second portion 918B appears displaced with respect to the first portion 918A by a displacement 920. Because the displacement 920 is generally an unknown value or vector, various techniques can be used such as to spatially register the first and second portions 918A and 918B. As shown in FIG. 9B, a spatially-registered slice 914C can include an adjusted location of a portion 918C of the target locus. Notationally, a set or series of acquired imaging slices can be labeled $S_i$, $S_{i-1}$, $S_{i-2}$, . . . , $S_{i-n}$, with $S_i$ corresponding to the most recently-acquired slice for processing and $S_{i-n}$ corresponding to the earliest-acquired slice for processing. A series of spatially-registered imaging slices can be labeled $S_i$, $S'_{i-1}$, $S'_{i-2}$, . . . $S'_{i-n}$.

FIG. 10 illustrates generally a technique that can include spatially registering segmented portions of a target locus from two (or more) imaging slices $S_i$, $S_{i-1}$, $S_{i-2}$, . . . , $S_{i-n}$. In one approach, a metric can be defined that quantifies how well the two portions of a target locus 1018A and 1018B are aligned (or more generally, how well two imaging slices or imaging volumes are aligned), such as the similarity between the pixels along the intersection line 1022 joining the first portion 1018A and the shifted second portion 1018B. Examples of such metrics include one-dimensional normalized cross-correlation or mutual information. An automated optimization technique can be executed to find translations of the second portion 1018B that provide the optimal value of the metric. Masks can be used to limit the calculation to the most relevant pixels only, such as pixels close to the target of interest. This first approach generally relies on the planes having a common intersection line.

Another approach can include creating three-dimensional (3D) voxel images, such as having a first image corresponding to a first slice orientation including populated voxels corresponding to a portion of the target locus within the slice and zero-valued voxels outside the slice, and a second image of a second slice orientation including its own populated voxels corresponding to the portion of the target locus in the second image. As an illustrative example, MR imaging slices generally have a finite thickness, such as corresponding to about 5 millimeters. A finite slice thickness can be taken into account by assigning voxels with slice information within the actual slice thickness using two-dimensional (2D) pixel information extracted from an MR imaging slice. A 3D registration technique can be used find the optimal translation between the two 3D images and masks can be used to exclude voxels that do not contain slice information. The 3D registration approach also generally relies on having a common intersection line. An illustrative example of three-dimensionally-registered imaging slices is shown illustratively in FIG. 11A.

In yet another approach, a prediction technique can be applied to a prior imaging slice to find the most likely position of a portion of the target locus for the prior imaging slice orientation but having the same time stamp as the current or a more-recently-acquired imaging slice. Various techniques can be used for such prediction, such as Kernel Density Estimation, a neural network, or a template matching technique. Prediction can be particularly effective if a motion of the target locus is highly periodic in nature, such as associated with respiratory motion. Although using a prediction is an approximation only, it can also be used in combination with the image-based methods described above and elsewhere herein. A prediction-based approach does not rely on image acquisition planes having a common intersection line, and so prediction techniques can be used when parallel slices are acquired.

In yet another approach, when fast perpendicular MR-imaging slices are acquired, dark lines can appear in the current image in the location where the previous image was excited and not yet fully relaxed to equilibrium. Because the excited magnetic dipoles from the previous slice follow the moving anatomy, a visible previously-excited region (e.g., an excitation line) can be used as an anchor to align previous slices with later-acquired imaging information. This can be taken into account implicitly with the other techniques mentioned above, because such darkened regions as pixel or voxel features can affect registration, or explicitly, such as by identifying or explicitly determining the location of such darkened regions in acquired imaging slices. For example, a peak-detection technique can be used to find points along the center of the darkened regions, and a line (straight or curved) can be found that provides a best fit to these points. Various examples described in this document refer to registration between images, such as including registration of a segmented portion of a first image with a segmented portion or other identified features of a second image (or a series of images). Generally, a registration between two images can include a moving and a fixed image. The goal can be to determine a position or transformation of the moving image such that it best fits the fixed image. "Move" can mean, for example, to shift the moving image spatially in one or more dimensions (translations only), shift and rotate the moving image, or even deform the moving image. The degrees of freedom available to move the moving image can be referred to as "optimization parameters," which, as an illustrative example, can include two degrees of freedom in the case of shift only with two 2D images, or 6 degrees of freedom for shifts plus rotations for 3D images. Even though we may be generally referring to 3D image registration, "optimization parameters" can still be generally referred to as "shift values" without loss of generality.

For a given set of optimization parameters, a metric can define a "goodness" of a determined overlap between the moving and fixed images. Various examples can include determining a normalized cross-correlation or mutual information (such as using voxel or pixel values as input values), and such techniques can provide an indication of an optimal value of the metric when the images match perfectly. The nature of the underlying imaging technique can be helpful in establishing which metric to use. For example, a mutual information technique can be used for images obtained using different modalities such as positron emission tomography (PET) and CT imaging.

An optimization technique can be used to find the shift values that optimize the metric between the moving and fixed images, such as to identify shift values that give the best match between the two images. Different optimizers that can be used can include gradient descent, simulating annealing, trust-region gradient descent, or one or more other techniques. In some cases, there may be deformations between the images, but it is not always necessary to optimize deformation vector fields and take these into account, because optimization of deformation information can result in one or more of undesired latency or can erode stability of the optimization technique. Calculation of the metric can be limited to a specified region of interest, such as referred to as a "mask." For example, assuming there is negligible deformation in the region of interest, one or more of translations or rotations, without deformation, can be used to determine shift values that are locally optimal in the specified region of interest.

Generally, if one or more 2D imaging slices are available, a motion of a radiation therapy target can be determined between a current 2D slice (such as an MR imaging slice) and an initial 3D volume (e.g., a reference volumetric image). As an illustrative example, the 3D volume can also correspond to a particular phase of respiration to reduce respiration blurring, which can be accomplished either with gated or triggered imaging (e.g., triggered imaging), or by extracting the 3D volumetric image from four-dimensional imaging information at a particular phase (e.g., extracting a 3D volumetric snapshot from a 4D imaging series, such as 4D imaging information obtained using MR imaging).

In one approach, the target itself can be identified in an imaging slice. However, while segmentation is mentioned elsewhere herein, the techniques described herein are also applicable if segmentation or other feature extraction is not performed. As an illustrative example, a best fit of grayscale values can be determined between one or more later-acquired imaging slices and an earlier-acquired reference 3D image. A target does not need to actually be in the image, but a region of interest can be specified, such as can include a portion of the target, or the target plus a margin, or just an arbitrary region of interest without the target.

In one approach, a 2D/3D registration can be performed to find a relative shift between a current imaging slice and the reference volume. The 3D image can represent the 'moving image' and a 2D slice can represent the 'fixed image' in relation to the registration technique. Generally, the location of target can be identified in the 3D image, and applying the relative shift to the earlier target location can provide an estimate of an updated location of the target, such as within a three-dimensional coordinate frame. Such an estimate can be performed without requiring determination of deformation, and may even be performed without use of rotational parameters, such as to increase execution efficiency of the optimization technique. Such simplifying assumptions can be applied such as when registering a 3D reference image to one or more 2D imaging slices.

A specified region of interest can be used to define a mask around the target plus a margin, for example (though the region of interest need not include the target or an entirety of the target). Deformation may be present, but as an illustrative example, if the margin is small, deformation will also be small (e.g., negligible) and a shift of the target itself can be determined using a registration technique ignoring deformation. In this manner, a single plane technique (e.g., a technique where the imaging slice is the fixed image) can still provide information indicative of a shift in three dimensions. Such a technique is robust when there are enough features in the images to "lock in" the registration in three dimensions—the registration converges to a well-defined optimum—though the features need not be extracted or segmented.

In one approach, a normalized cross-correlation of the gradient of the images can be used as a registration metric, since such a technique tends match images edges and is less sensitive to absolute grayscale values that can differ from image to image. A single imaging slice or plane may, in some cases, not be sufficiently robust to establish a shift with a clear optimal value (colloquially, 'lock in'). Accordingly, additional slices can be useful to help lock in all directions, for example using a current sagittal and a previously-acquired coronal slice, or vice-versa, as illustrative examples. As a count of slices used for registration increases, whether parallel, orthogonal, or in non-parallel and non-orthogonal planes, more information is available to perform a registration between the reference volumetric image and the later-acquired imaging slices, which improves the robustness of the resulting shift parameter determination.

The registration can include sweeping a 3D volume across one or more imaging slices, or the slices can be inserted into a 3D volume as mentioned elsewhere herein, in which case a 3D-to-3D registration technique can be used (such as suppressing or ignoring registration of unfilled voxels). A multiple-slice technique works well such as if the slices are acquired in rapid succession, for example, less than about 50 ms between instants corresponding to acquired slices. If a longer duration occurs between imaging slice acquisitions, then the older slices may become 'stale.' However, such slices can still be temporally re-aligned such as using either a) a prediction technique, such as where the target motion is periodic in nature; b) aligning the excitation lines provided by the imaging modality (e.g., excitation lines visible from MR imaging acquisition), for example by fitting a line through such excitation lines as mentioned elsewhere herein; or c) by spatially-registering the stale imaging slice so that it fits with the current slice using a metric that is calculated along a line of intersection.

FIG. 11A illustrates generally a composite 1118 representation of a target locus, such as after spatial registration of segmented portions of the target locus acquired at different times corresponding to spatially-registered imaging slices 1114A and 1114B. After portions of the target locus from two or more imaging slices have been spatially registered, a feature can be extracted such as from a composite 1118. For example, a centroid location 1108 of the composite 1118 or other feature can be determined, such as providing an estimate of a centroid location of the target locus for use in updating a radiation therapy protocol. In another example, a determined spatial displacement between portions of the target locus in the first and second imaging slices 1114A and 1114B can be used to update a radiation therapy protocol.

FIG. 11B illustrates generally a technique for determining a difference between a later estimated or predicted location of a composite 1118 of the target locus according to acquired spatially-registered imaging information as compared to an earlier location of the target locus 616 such as represented by earlier-acquired volumetric imaging information. A displacement of one or more features can be used to estimate a present or future target locus location. For example, a displacement can be determined between an earlier-determined centroid 608 extracted from the reference imaging information and later-determined centroid 1108. In another example, shift parameters from an imaging registration can be used to provide an updated target locus without requiring extraction or determination of features such as a centroid. Generally, a variety of other techniques can be used such as to extract information indicative of a motion or displacement of the target locus 616 using spatially-registered imaging slices.

For example, once a set of previous imaging slices are aligned to the current slice to form a slice set $S_i$, $S'_{i-1}$, $S'_{i-2}$, . . . $S'_{i-n}$, an optimal registration between the slice set (or a composite 1108 generated from such a slice set) and a three-dimensional reference volume can be found (such as a reference volume corresponding to the target locus 616 as shown in FIG. 11B). As an illustrative example, a sagittal slice acquisition can be preceded by a coronal slice acquisition. A spatial translation can be identified that brings the coronal slice to the same time point as the sagittal slice to spatially register the coronal slice with the sagittal slice. Then, both slices can be established within a 3D voxel coordinate space. This can be done by inserting the slices as infinitesimally thin slices, or as finite slices using the known slice thickness (such as shown in the composite 1118 of FIG. 11A and FIG. 11B).

Voxels that are not filled by portions of the target locus from each slice can be left unfilled. A 3D-to-3D registration can then be determined between the 3D reference image (e.g., corresponding to target locus 616) and the 3D "slice-filled image" (corresponding to the composite 1118). A mask can be used to filter out voxels that have not been filled. In another example, a 3D-to-2D registration can be performed, such as using multiple 2D slices rather than a single composite. For example, shift parameters (e.g., displacement of one or more features such as a centroid or a set of shift values specifying a translation or rotation of region of interest) of the 3D reference image can be evaluated, such as optimizing values of a similarity metric that compares the voxels of the shifted 3D volumetric reference image to each of the slices of the multiple 2D imaging slices, using registration and optimization techniques as mentioned above. In this manner, a 3D-to-2D registration can be performed, such as to identify an optimal set of shift values. A location of the target can be updated using information obtained from the shift values. 3D-to-3D, 2D-to-2D, or 3D-to-2D registration techniques need not require image segmentation (e.g., the target locus itself need not be segmented), and such registration need not require identification of imaging features such as a centroid or edge location. Instead, registration can be performed using grayscale or contrast imaging information (or other extracted values), such as over a specified region of interest generally as mentioned elsewhere herein FIG. 11C illustrates generally a technique for updating a therapy protocol, such as to shift a therapy locus to a new location. An earlier radiation therapy target region 1110A can be established, such as corresponding to a target locus extracted from a volumetric reference image or established according to other treatment or dosimetric objectives. Such a therapy target region 1110A can be established at least in part using one or more of positioning a radiation therapy output, modulating a therapy beam including modulating one or more of intensity or beam shape, or moving the patient using an actuator such as a moveable therapy couch or platform. One or more features can be extracted from the therapy target region, such as a centroid 1108A. An estimated or predicted displacement of the target locus (e.g., a tumor or other structure to be treated) can be determined, such as using other techniques as described herein.

The therapy target region 1110A can be adjusted to provide an updated therapy target region 1110B. For example, if the target locus has been translated due to patient motion, a similar displacement can be applied to the earlier centroid 1110A to provide an updated therapy target region 1110B centroid 1108B. Similarly, if other features are extracted, the therapy target region 1110A can be adjusted using other techniques such as rotation or scaling. In another example, instead of or in addition to adjusting the therapy target region 1110A, other techniques can be used to control therapy, such as gating therapy to inhibit delivery of radiation therapy unless an updated therapy target region 1110B falls within a specified zone. In yet another example, a surrogate signal, such as derived from a sensor output, can be used to gate therapy. For example, a sensor output can be correlated with the location of a feature extracted from imaging slices, such as a centroid location of a target locus within the imaging slices after the imaging slices are spatially-registered. Therapy delivery can be gated in a synchronous manner, such as triggered in response to the sensor output (e.g., such as to deliver therapy at a certain time during a periodic motion such as respiration).

Figure 12:
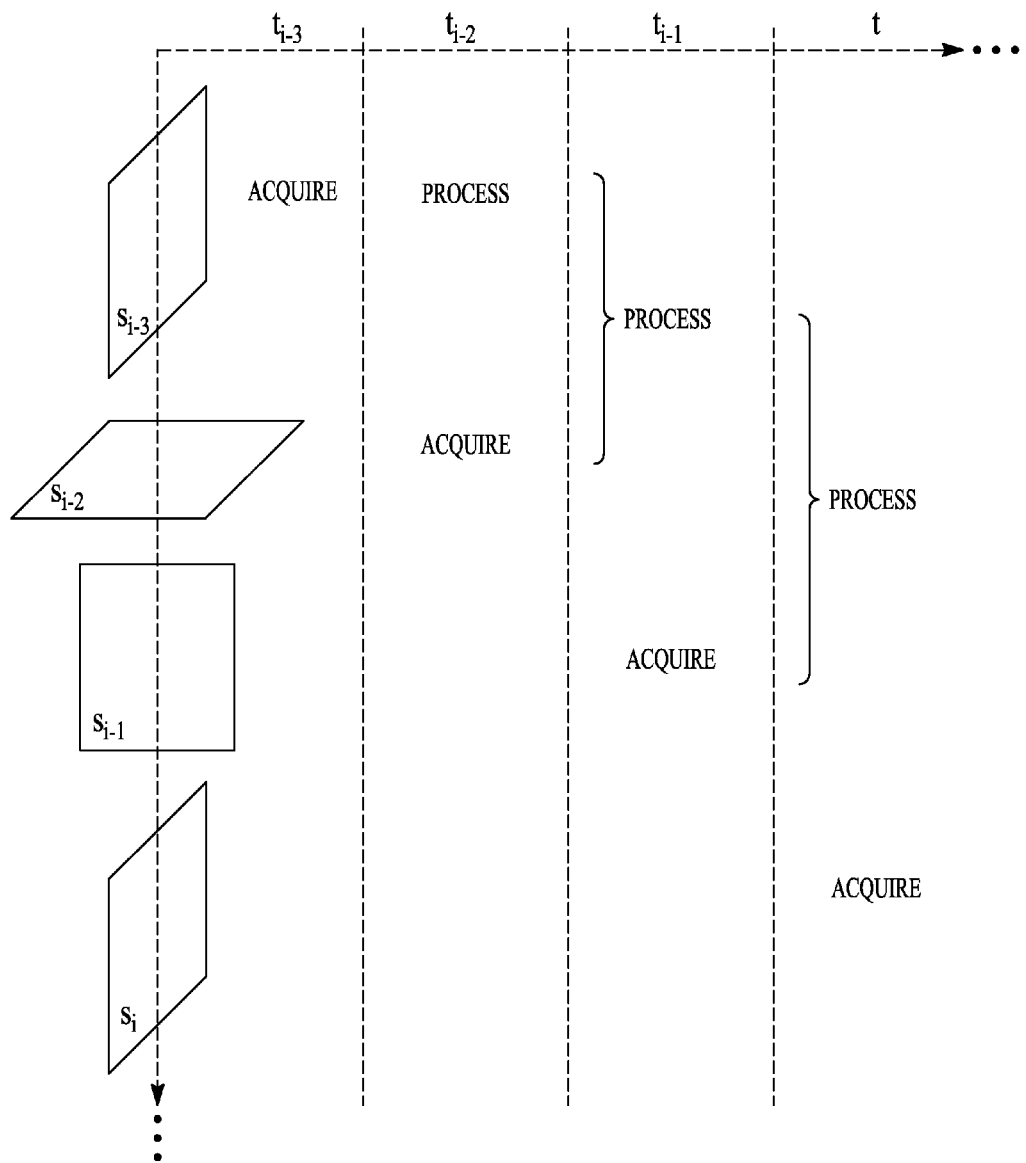
FIG. 12 illustrates a technique that can include interleaving processing of imaging information corresponding to previously-acquired imaging slices with imaging acquisitions, such as to enhance efficiency of other techniques described herein.

The techniques described above can be performed in a serial manner, such as including acquiring images and processing such images, then acquiring another series of images, and processing the subsequently-acquired set of images. In another approach, one or more portions of the techniques described herein can be performed in parallel or in an interleaved manner, such as to provide ongoing generation of displacement or other information for use in updating a therapy protocol in an adaptive manner. For example, FIG. 12 illustrates a technique that can include interleaving processing of imaging information corresponding to previously-acquired imaging slices with imaging acquisitions, such as to enhance efficiency of other techniques described herein. An imaging acquisition system can acquire imaging slices, such as slices $S_i$, $S_{i-1}$, $S_{i-2}$, $S_{i-3}$, ... corresponding to acquisition times $t_i$, $t_{i-1}$, $t_{i-2}$, $t_{i-3}$, ... as shown illustratively in FIG. 12. At time t, the slice $S_i$ can be acquired and one or more previously-acquired slices, such slices $S_{i-1}$ and $S_{i-2}$ can be spatially registered to each other or otherwise processed during acquisition of the imaging slice $S_i$.

As an illustrative example, the imaging slices are shown as two-dimensional planes that are orthogonal to each other. However, as mentioned in relation to other examples herein, the slices need not be planar nor orthogonal. Each acquired imaging slice can be processed, including processing of one or more slices in parallel with an acquisition of an imaging slice. For example, such processing can include sampled information from a volumetric reference image, such as corresponding to a plane or region of the acquired imaging slice. The extent of a target locus (e.g., a tumor or other anatomical structure that can be used as a landmark for adaptively directing radiation therapy) can be extracted from one or more segmented structures in the volumetric reference image.

A margin can be added to that extent of the target locus, such as to define a region within which the target locus must be located in subsequently-acquired imaging slices. The margin can be adjusted based on factors such as an image acquisition rate (the lower the acquisition rate, the farther the tumor or other target can travel between image acquisitions and the margin can be correspondingly enlarged). The tumor or other target can be segmented in an acquired imaging slice. Segmented target information extracted from one or more imaging slices can be spatially-registered with the target locus identified in the planning image. Such registration, as described in other examples herein, can be used to determine an updated target locus or to otherwise control or adapt therapy. For example, the updated target locus can be used to gate the treatment, such as pausing the treatment while the updated target locus indicates that the target locus is partially or entirely outside a specified spatial gating window, or the updated target locus can be used to adapt the beam aperture shape to track the tumor, as illustrative examples.

While performing such processing, previously-acquired imaging slices can be re-used, such as to make gating or tracking updates at a higher rate, such as shown illustrative in FIG. 12. Information about the update target locus, such as an extracted feature location (e.g., a centroid location) can be used to adjust a location or orientation of future acquired imaging slices, such as to re-center or otherwise keep a desired portion of the target locus within the imaging field.

Figure 13:
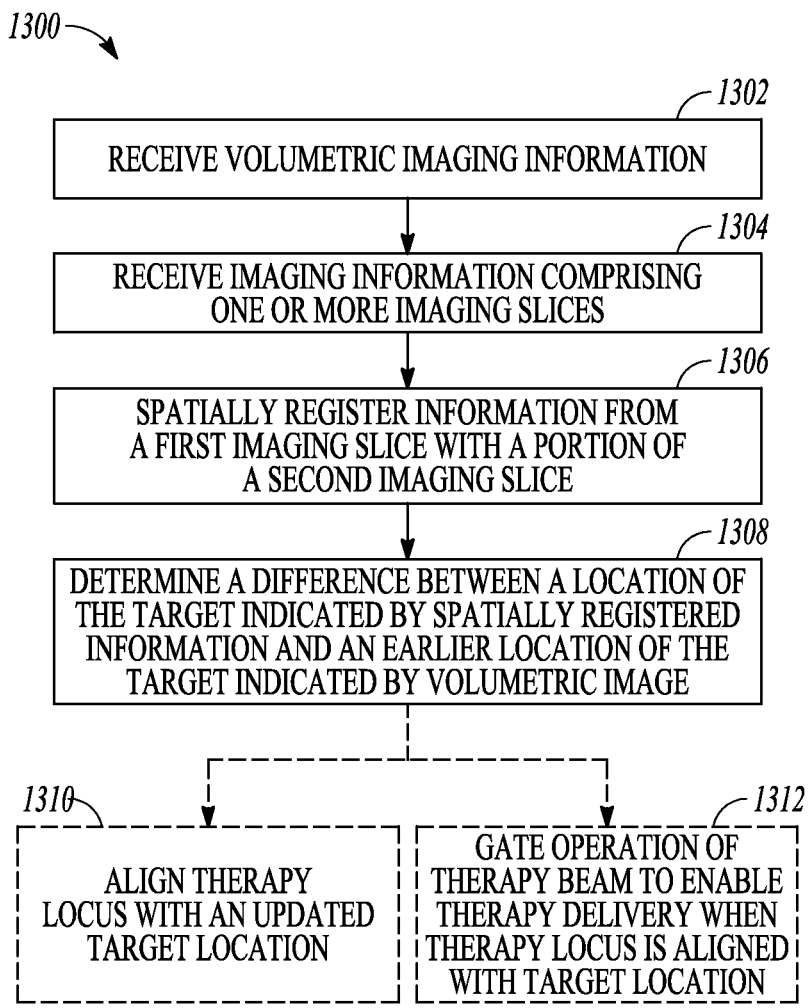
FIG. 13 illustrates generally a technique, such as a method, that can include receiving volumetric imaging information, such as a reference image, and receiving imaging slices, including determining a difference in the location of the target locus.

FIG. 13 illustrates generally a technique 1300, such as a method, that can include receiving volumetric imaging information at 1302, such as a reference image, and receiving imaging slices 1304, including determining a difference in the location of the target locus at 1308. A portion or an entirety of the technique 1300 (or other techniques described herein) can be performed such as using a system or other elements as shown in FIG. 1A, FIG. 1B, FIG. 1C, FIG. 1D, FIG. 2, FIG. 3, FIG. 4 or FIG. 5.

At 1302, volumetric imaging information can be received, such as corresponding to a planning or reference image. The volumetric imaging information can include a target locus, such as comprising a region of voxels to be targeted with a radiation therapy. As mentioned elsewhere herein, an imaging acquisition latency may preclude obtaining full volumetric imaging of the target locus in a real-time manner, such as intra-fractionally. Accordingly, at 1304, imaging information can be received such as comprising one or more imaging slices. For example, two imaging slices can be acquired, such as at different time periods different instants after acquisition of the volumetric image received at 1302. If the two imaging slices are acquired at different times, a location of a portion of the target locus in each of the imaging slices can be different (and such imaging slices can be referred to as "temporally misaligned").

At 1306, if the imaging slices are temporally misaligned, information (such as indicative of the target locus) from an earlier-acquired one of the at least two imaging slices can be spatially registered with at least a portion of a later-acquired one of the at least two imaging slices. At 1308, a difference can be determined between a location of the target locus indicated by the spatially registered information and an earlier location of the target locus indicated by the volumetric image received at 1302. For example, a registration technique can be used as mentioned above, such as to determine a shift in a feature such as a centroid of the target locus or a shift in the target without requiring segmentation or feature extraction. Determined shift values can provide information indicative of an updated location of the target or other region of interest.

Optionally, at 1310, a therapy locus (e.g., an area or volume targeted by a radiation therapy beam) can be updated using information about the updated location of the target determined at 1308. In addition, or instead, optionally, at 1312, the therapy beam operation can be gated, such as to enable therapy delivery when the therapy is properly aligned with the updated or estimated target location. In this manner, a radiation therapy treatment can be adaptively controlled using imaging slices and an earlier-acquired volumetric reference image.

Various Notes & Examples

Each of the non-limiting examples described in this document can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A computer-implemented method of controlling an adaptive radiation therapy delivery system, the method comprising:
   receiving an inter-fractional volumetric image comprising a time-varying target locus, the inter-fractional volumetric image acquired at a first time period;
   receiving at least two intra-fractional imaging slices comprising different portions of the target locus, wherein a first intra-fractional imaging slice is acquired at a second time period and a second intra-fractional imaging slice is acquired at a third time period and wherein the at least two intra-fractional imaging slices are received contemporaneously within the same fractional radiation session with a delivered radiation therapy and are in different image planes having different orientations;
   spatially registering a portion of the target locus from the first intra-fractional imaging slice and a portion of the target locus from the second intra-fractional imaging slice, including translating a portion of the target locus in the second intra-fractional imaging slice to register a portion of the target locus in the second intra-fractional imaging slice with a portion of the target locus in the first intra-fractional imaging slice;
   determining a difference between a location of the target locus indicated by the spatially-registered information and the target locus indicated by the inter-fractional volumetric image; and
   generating an updated therapy protocol to control delivery of a therapy beam based on the determined difference.

2. The computer-implemented method of claim 1, wherein the first time period is earlier than the second and third time periods.

3. The computer-implemented method of claim 1, wherein the second and third time periods are different.

4. The computer-implemented method of claim 1, wherein generating the updated therapy protocol includes aligning a therapy locus to which the therapy beam is directed with an updated target locus.

5. The computer-implemented method of claim 1, wherein generating the updated therapy protocol includes gating operation of the therapy beam to enable therapy delivery when the therapy locus is aligned with the location of the target locus.

6. The computer-implemented method of claim 1, wherein the portions of the target locus included in the at least two imaging slices partially overlap.

7. The computer-implemented method of claim 1, wherein the portions of the target locus included in the at least two imaging slices do not overlap.

8. The computer-implemented method of claim 1, wherein spatially registering the information indicative of the portions of the target locus includes segmenting the portion of the target locus in the at least two imaging slices.

9. The computer-implemented method of claim 8, wherein spatially registering the information indicative of the portions of the target locus includes translating a segmented portion of the target locus in one or more earlier-acquired image slices to register the segmented portion of the target locus with a segmented portion of the target locus from a later-acquired image slice.

10. The computer-implemented method of claim 8, wherein spatially registering the information indicative of the portions of the target locus in one or more earlier-acquired image slices includes predicting a location of a segmented portion of the target locus from an earlier-acquired image slice corresponding to an instant of acquisition of a later-acquired imaging slice.

11. The computer-implemented method of claim 1, wherein determining a difference between a location of the target locus indicated by the spatially-registered information and the location of the target locus indicated by the volumetric image comprises:
   segmenting the target locus in the volumetric image; and
   generating a three-dimensional voxel representation of the spatially-registered information indicative of the target locus from the at least two imaging slices.

12. The computer-implemented method of claim 11, wherein determining a difference between a location of the target locus comprises spatially registering the segmented target locus from the volumetric image with the three-dimensional voxel representation from the at least two imaging slices.

13. The computer-implemented method of claim 1, wherein the imaging slices comprise one-dimensional imaging profiles.

14. The computer-implemented method of claim 1, wherein imaging slices comprise two-dimensional imaging information.

15. The computer-implemented method of claim 1, wherein the imaging slices are planar.

16. The computer-implemented method of claim 15, wherein the imaging slices are orthogonal.

17. The computer-implemented method of claim 1, wherein the imaging slices are parallel.

18. The computer-implemented method of claim 1, wherein determining a difference between the location of the target locus indicated by the spatially-registered information and the earlier location of the target locus indicated by the earlier-acquired volumetric image occurs concurrently with an image acquisition of another imaging slice.

19. The computer-implemented method of claim 1, wherein the imaging information is obtained using nuclear magnetic resonance (MR) imaging.

20. The computer-implemented method of claim 1, wherein the imaging information is obtained using computed tomography (CT) imaging.

21. The computer-implemented method of claim 1, wherein the imaging information obtained using ultrasound imaging.

22. The computer-implemented method of claim 1, further comprising determining a metric indicative of an alignment between the portion of the target locus from the first intra-fractional imaging slice and the portion of the target locus from the second intra-fractional imaging slice and adjusting a position of the second intra-fractional imaging slice to improve an alignment between the portion of the target locus from the first intra-fractional imaging slice and the portion of the target locus from the second intra-fractional imaging slice.

23. The computer-implemented method of claim 22, wherein determining a metric indicative of an alignment between the portion of the target locus from the first intra-fractional imaging slice and the portion of the target locus from the second intra-fractional imaging slice includes masking a portion of the first intra-fractional imaging slice and the second intra-fractional imaging slice.

24. The computer-implemented method of claim 22, wherein determining a metric indicative of an alignment between the portion of the target locus from the first intra-fractional imaging slice and the portion of the target locus from the second intra-fractional imaging slice includes determining a similarity between a line of intersection between the portion of the target locus from the first intra-fractional imaging slice and the portion of the target locus from the second intra-fractional imaging slice.

25. An adaptive radiation therapy delivery system, comprising:
   a therapy generator configured to deliver a therapy beam to be directed to a therapy locus;
   a therapy controller system coupled to the therapy generator, the therapy controller system comprising an imaging input, the therapy controller system configured to:
   receive an inter-fractional volumetric image comprising a time-varying target locus; and
   receive at least two intra-fractional imaging slices contemporaneously within the same fractional radiation session with the delivered therapy beam, the at least two intra-fractional imaging slices comprising different portions of the target locus and being in different image planes having different orientations;
   spatially register a portion of the target locus included in one of the at least two intra-fractional imaging slices with a portion of the target locus included in another one of the at least two intra-fractional imaging slices and translate a portion of the target locus in one of the intra-fractional imaging slices to register a portion of the target locus in the intra-fractional imaging slice with a portion of the target locus in the other of the intra-fractional imaging slices;
   determine a difference between a location of the target locus indicated by the spatially-registered information and a location of the target locus indicated by the volumetric image; and
   generate an updated therapy protocol to control delivery of a therapy beam based on the determined difference.

26. The adaptive radiation therapy delivery system of claim 25, wherein the at least two imaging slices are acquired after acquisition of the volumetric image.

27. The adaptive radiation therapy delivery system of claim 26, wherein the at least two imaging slices are acquired at different time periods.

28. The adaptive radiation therapy delivery system of claim 25, wherein the therapy controller system is configured to generate the updated therapy protocol including aligning a therapy locus to which the therapy beam is directed with an updated target locus.

29. The adaptive radiation therapy delivery system of claim 25, wherein the therapy controller system is configured to generate the updated therapy protocol including gating operation of the therapy beam to enable therapy delivery when the therapy locus is aligned with the location of the target locus.

30. The adaptive radiation therapy delivery system of claim 25, further comprising a nuclear magnetic resonance (MR) imaging system; and
   wherein the imaging information is obtained using MR imaging performed by the MR imaging system.

31. The adaptive radiation therapy delivery system of claim 25, further comprising an X-ray imaging system; and
   wherein the imaging information is obtained using computed tomography (CT) imaging performed using the X-ray imaging system.

32. The adaptive radiation therapy delivery system of claim 25, further comprising an ultrasound imaging system; and
   wherein the imaging information is obtained using the ultrasound imaging system.

* * * * *